(12) United States Patent
Sancoff et al.

(10) Patent No.: US 11,016,070 B2
(45) Date of Patent: May 25, 2021

(54) SYSTEM FOR ASSESSING THE QUALITY OF AIR AND DRINKING WATER

(71) Applicant: Live-Pure, Inc., Newington, NH (US)

(72) Inventors: Greg Sancoff, North Hampton, NH (US); Blake Sancoff, North Hampton, NH (US); Joel Nevin, Portsmouth, NH (US)

( * ) Notice: Subject to any disclaimer, the term of this patent is extended or adjusted under 35 U.S.C. 154(b) by 224 days.

(21) Appl. No.: 16/029,234

(22) Filed: Jul. 6, 2018

(65) Prior Publication Data

US 2019/0011419 A1 Jan. 10, 2019

Related U.S. Application Data

(60) Provisional application No. 62/633,241, filed on Feb. 21, 2018, provisional application No. 62/529,145, filed on Jul. 6, 2017.

(51) Int. Cl.
| | |
|---|---|
| *G01N 1/10* | (2006.01) |
| *G01N 1/22* | (2006.01) |
| *G01N 1/24* | (2006.01) |
| *G01N 1/26* | (2006.01) |
| *G01N 33/18* | (2006.01) |

(Continued)

(52) U.S. Cl.
CPC ............ *G01N 33/0075* (2013.01); *G01N 1/14* (2013.01); *G01N 1/2202* (2013.01);
(Continued)

(58) Field of Classification Search
CPC .. G01N 1/10; G01N 1/14; G01N 1/22; G01N 1/2202; G01N 1/2205; G01N 1/2208; G01N 1/2211; G01N 1/2214; G01N 1/2273; G01N 1/24; G01N 2001/2217; G01N 2001/222; G01N 2001/223; G01N 2001/2276; G01N 2001/241; G01N 2001/245; G01N 33/0004; G01N 33/0009; G01N 33/0073; G01N 33/0075; G01N 33/18; G01N 33/1806; G01N 33/1813; G01N 33/182; G01N 33/1826; G01N 33/1833; G01N 2033/184; G01N 35/00584; G01N 35/00732; G01N 35/00742; G01N 35/00752;

(Continued)

(56) References Cited

U.S. PATENT DOCUMENTS

| | | | |
|---|---|---|---|
| 5,419,209 A | 5/1995 | Sepe | |
| 5,630,935 A * | 5/1997 | Treu | ............... A61L 2/04 210/130 |

(Continued)

*Primary Examiner* — Herbert K Roberts
(74) *Attorney, Agent, or Firm* — Pandiscio & Pandiscio

(57) ABSTRACT

A system for assessing the quality of air and/or drinking water, the system comprising a plurality of sample traps, wherein each of the sample traps is configured to test for a different environmental contaminant; a base unit having a pump for drawing air, a mount for connecting a sample trap to the pump so as to draw air through that sample trap when the pump is operated, a central processing unit (CPU) pre-programmed to operate the pump in a plurality of modes of operation, and a plurality of buttons communicating with the CPU; and a marking scheme comprising a plurality of unique markings, wherein each of the buttons is marked with a different unique marking, and further wherein each of the sample traps is marked with the same unique marking as the button which causes the pump to operate in a particular mode of operation.

45 Claims, 27 Drawing Sheets

(51) Int. Cl.
 *G01N 35/00* (2006.01)
 *G01N 35/10* (2006.01)
 *G01N 33/00* (2006.01)
 *G01N 1/14* (2006.01)

(52) U.S. Cl.
 CPC .............. *G01N 1/2273* (2013.01); *G01N 1/24* (2013.01); *G01N 33/18* (2013.01); *G01N 35/0092* (2013.01); *G01N 35/00732* (2013.01)

(58) Field of Classification Search
 CPC ....... G01N 35/00762; G01N 35/00772; G01N 35/00782; G01N 35/00792; G01N 35/00801; G01N 35/00811; G01N 35/00821; G01N 35/00831; G01N 35/00851; G01N 35/00861; G01N 35/0092
 See application file for complete search history.

(56) References Cited

U.S. PATENT DOCUMENTS

| | | | |
|---|---|---|---|
| 6,564,655 B1 * | 5/2003 | Austen | G01N 1/14 73/863.01 |
| 6,672,134 B2 | 1/2004 | Bodnar | |
| 6,711,525 B1 * | 3/2004 | Fox | B01D 35/143 702/184 |
| 7,155,988 B2 | 1/2007 | Cole | |
| 7,511,809 B2 | 3/2009 | Schneider et al. | |
| 8,146,448 B2 | 4/2012 | Briscoe et al. | |
| D834,433 S | 11/2018 | Tackett | |
| 2006/0189895 A1 * | 8/2006 | Neel | A61B 5/150358 600/584 |
| 2006/0286606 A1 | 12/2006 | Oliver | |
| 2007/0108135 A1 * | 5/2007 | Davis | B67D 3/0009 210/760 |
| 2008/0063570 A1 * | 3/2008 | Fujino | G01N 35/00732 422/400 |
| 2009/0318276 A1 * | 12/2009 | Miller | G01N 35/0092 494/20 |
| 2012/0074214 A1 * | 3/2012 | Mizumoto | G01N 35/00663 235/375 |
| 2013/0017110 A1 | 1/2013 | Villagomez et al. | |
| 2015/0276773 A1 * | 10/2015 | Aoki | G05B 15/02 700/90 |
| 2016/0116405 A1 | 4/2016 | Bertaux | |
| 2017/0156550 A1 | 6/2017 | Ciavarella et al. | |
| 2019/0000365 A1 * | 1/2019 | Beyerlein | A61B 5/150022 |

* cited by examiner

Contents:
- 1 *yogi*™ sampling instrument
- 1 12-volt power supply
- 1 chain of custody form
- 1 sample box with shipping label, containing:
  - 1 temperature indicator
  - 1 humidity level indicator
  - 1 blue capsule with adaptor.
  - 2 white capsules with water bottles.
  - 2 red capsules with radon traps.
  - 2 yellow capsules with spore traps.
  - 2 orange capsules with dust and fiber traps.
  - 1 green capsule with tube.
  - 1 indigo capsule with tube.

FIG. 2

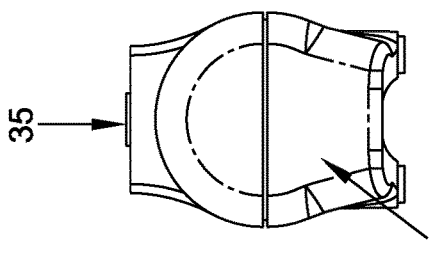
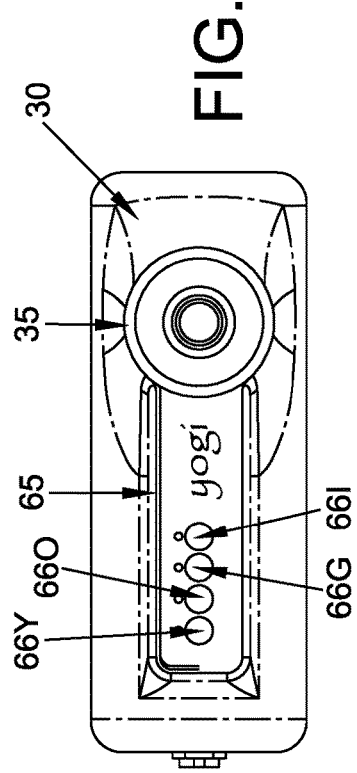
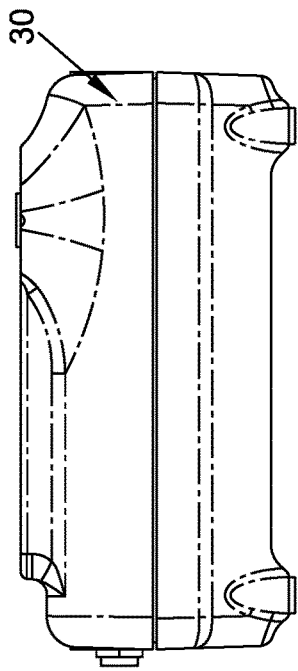
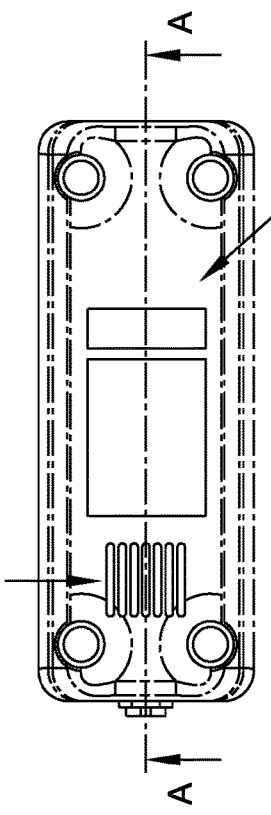
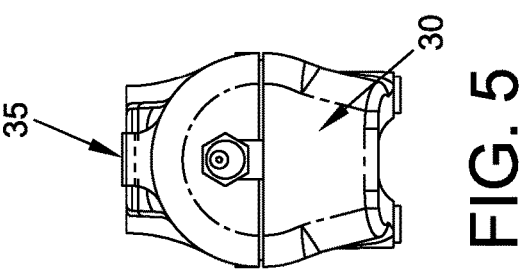

Radon Sample

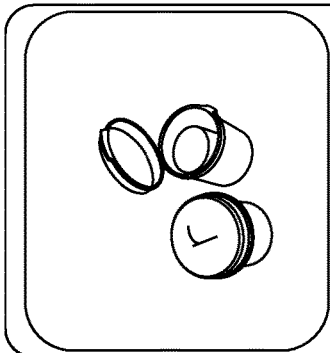

This test should be performed in the lowest level of the building. Close all windows and doors to the testing area 12 hours prior to the test.

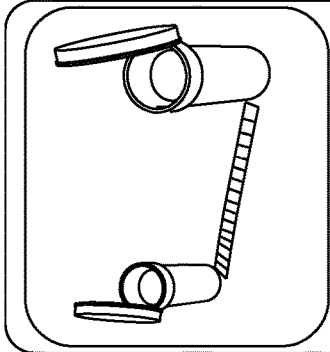

Remove the humidity strip and the temperature strip from the sample box.

Select the two red capsules from the sample box.

Open the caps.

Place the capsules as shown about five inches apart in the lowest level of the building and leave as shown for 48 hours.

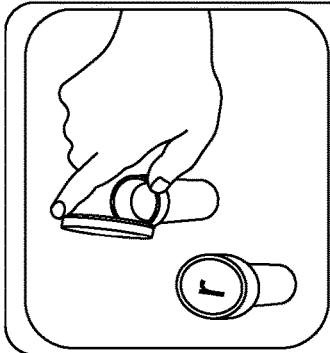

Close all windows and doors at this level of the building. Do not disturb for 48 hours.

After 48 hours, close the lids and place back in the sample box.

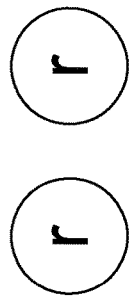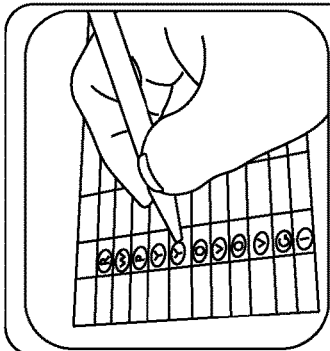

Check the box next to the red circle on the chain of custody form.
Record the humidity level indicated in pink on the test strip.
Record the approximate temperature indicated in green on the thermometer strip.

(This test should be received by the lab within five days of completion for best results.)

FIG. 24

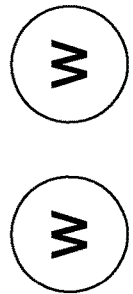
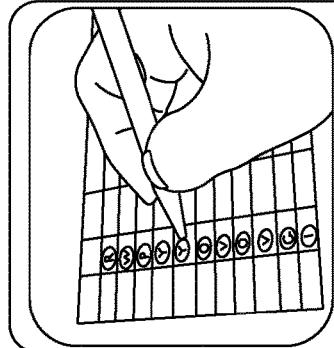
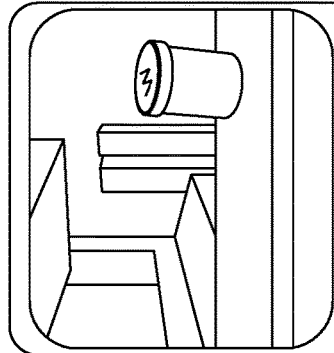
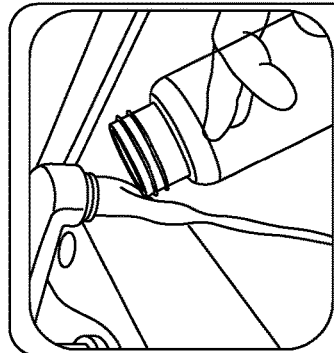
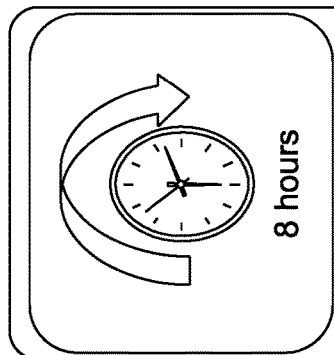
FIG. 25

Outdoor Air Sample

The sampling instrument works best when started at room

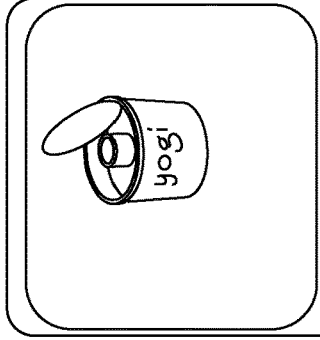

Select the yellow capsule marked "outdoor" from the sample box.

Remove the spore trap.

Peel off the seals from both ends.

(Retain for later use)

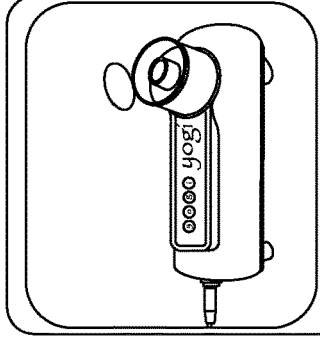

Place the sampling instrument outside about three feet from the ground on a day when there is no precipitation.

Plug the instrument into an electrical outlet.

Load the spore trap onto the hub with the arrow pointing down.

Press firmly.

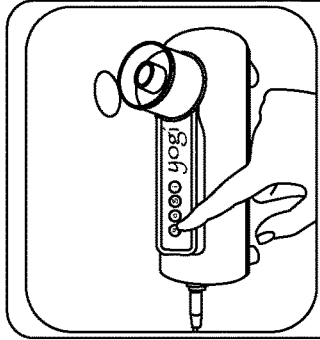

Push the yellow button marked "y" on the keypad

The instrument will run for five minutes, beep and shut off.

Remove the spore trap from the hub.

Replace the seals.

Return the spore trap to the capsule, close the lid and place back in the sample box.

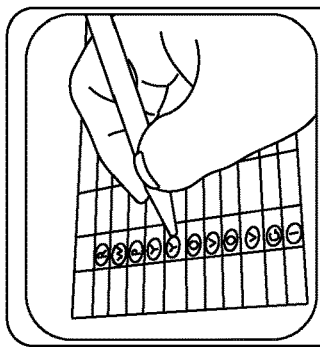

Check the box next to the yellow circle marked "outdoor" on the chain of custody form.

FIG. 26

Indoor Air Sample

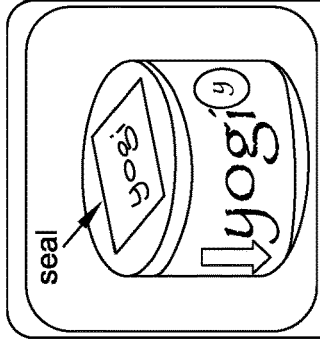

Select the yellow capsule marked "indoor" from the sample box.

Remove the spore trap.

Peel off the seals from both ends.

(Retain for later use.)

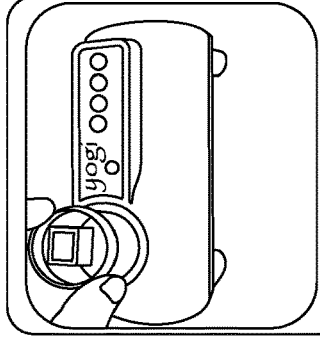

Place the instrument in the desired testing area.

Place the sampling instrument approximately three feet from the floor.

Plug the instrument into an electrical outlet.

Load the spore trap onto the hub with the arrow pointing down.

Press firmly.

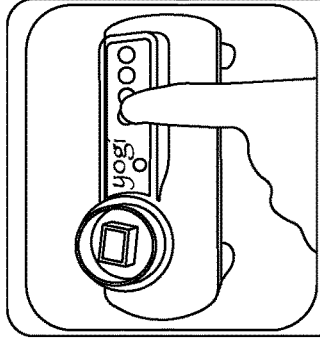

Push the yellow button marked "y" on the keypad.

The instrument will run for five minutes, beep and shut off.

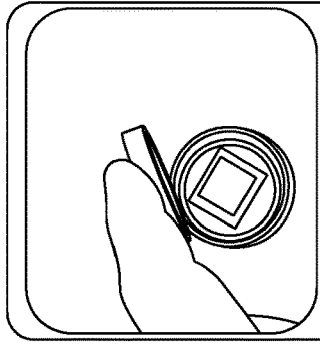

Remove the spore trap from the hub.

Replace the seals.

Return the spore trap to the capsule, close the lid and place back in the sample box.

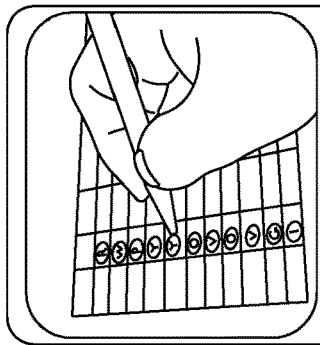

Check the box next to the yellow circle marked "indoor" on the chain of custody form.

FIG. 27

Asbestos Air Sample

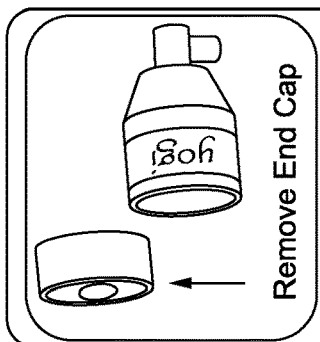

Remove End Cap

Select the orange capsule marked "asbestos" from the sample box.

Remove the fiber trap from the capsule.

Pull off the end cap.

(Retain for later use.)

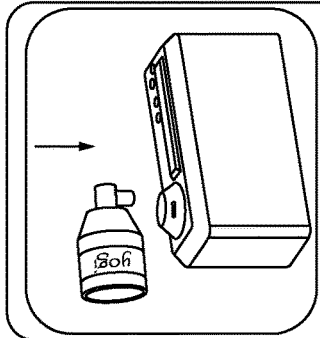

Load the fiber trap onto the hub as shown.

Press firmly.

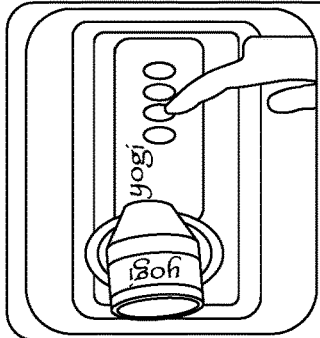

Push the orange button marked "o" on the keypad.

The instrument will run for 15 minutes, beep and shut off.

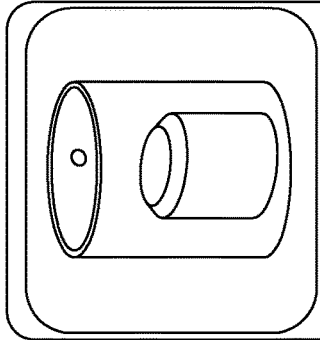

Remove the fiber trap from the hub.

Replace the end cap.

Return the trap to the capsule, close the lid and place back in the sample box.

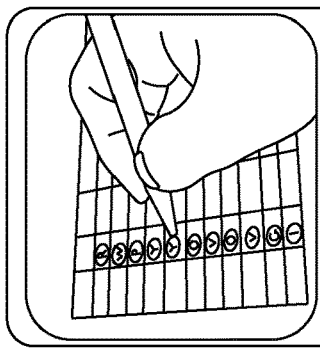

Check the box next to the orange circle marked "asbestos" on the chain of custody form.

FIG. 28

VOCs Air Sample

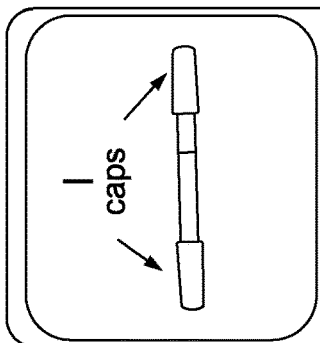

- Select the indigo capsule from the sample box.
- Remove the glass tube.
- Take the caps off both ends.

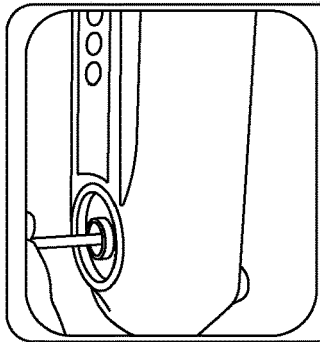

- Insert the tube into the hub with the arrow pointing down.
- Press gently until the tube stops.

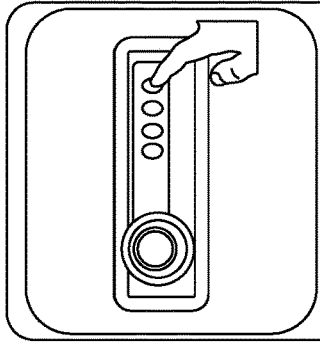

- Push the indigo button marked "i" on the keypad.
- The instrument will run for 2 hours, beep and shut off.

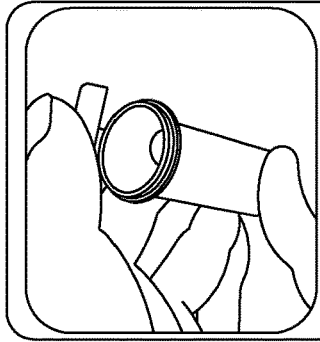

- Remove the tube from the hub.
- Replace both caps.
- Return the tube to the capsule, close the lid and place back in the sample box.

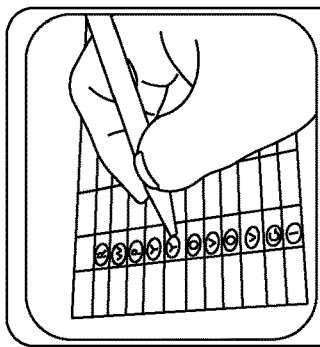

- Check the box next to the indigo circle on the chain of custody form.
- Retain the adaptor for future use.

FIG. 32

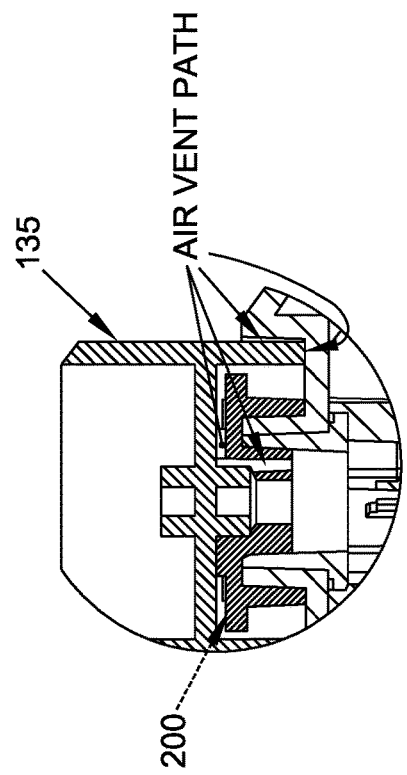
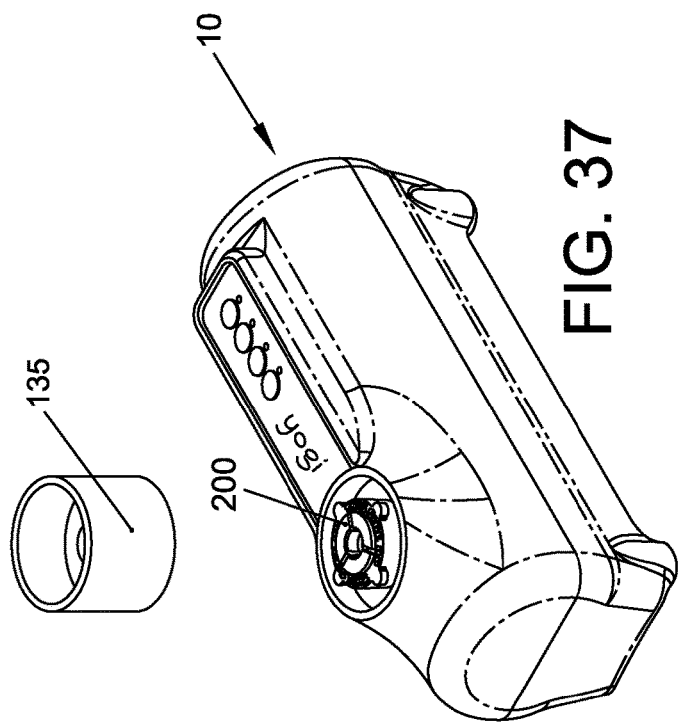
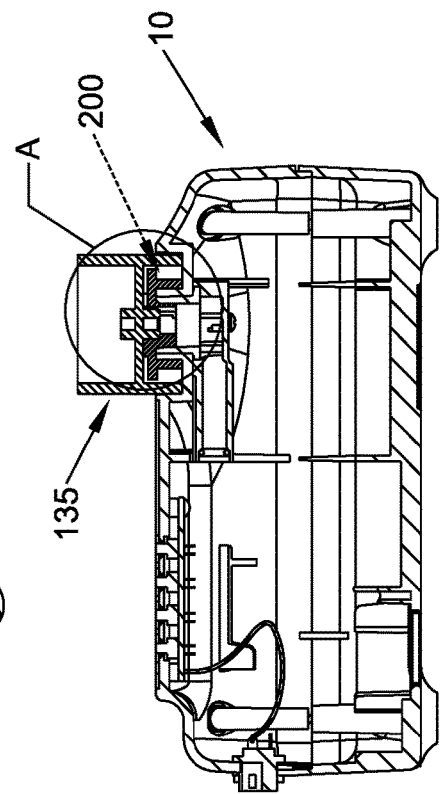

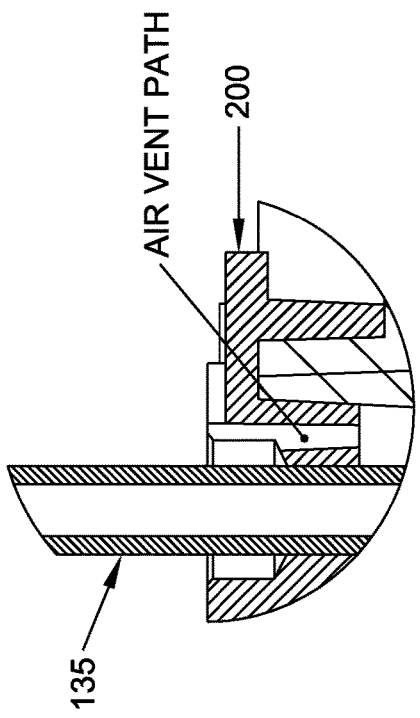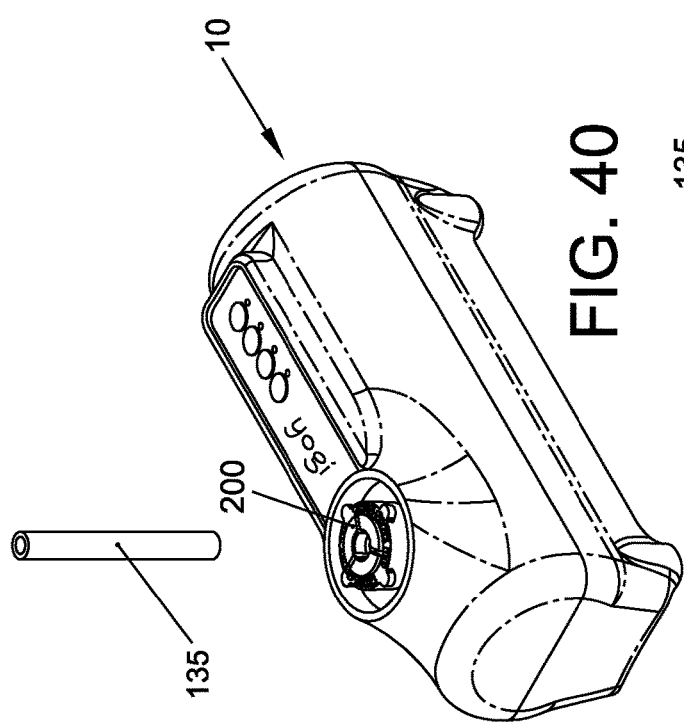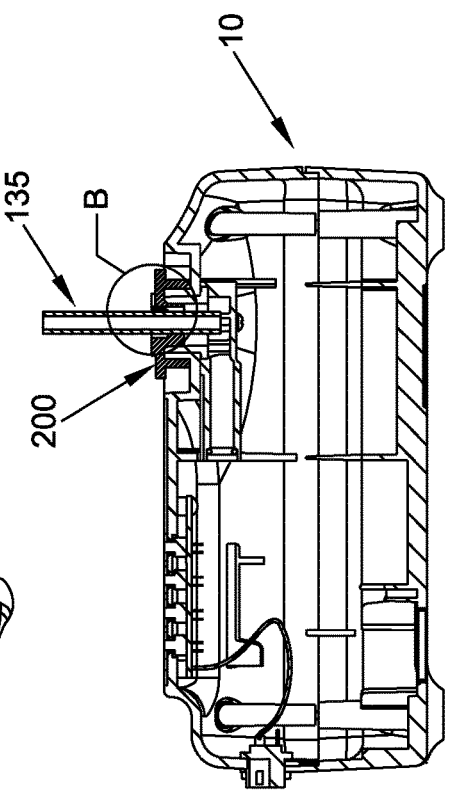

SYSTEM FOR ASSESSING THE QUALITY OF AIR AND DRINKING WATER

REFERENCE TO PENDING PRIOR PATENT APPLICATIONS

This patent application claims benefit of:

(i) U.S. Provisional Patent Application Ser. No. 62/529,145, filed Jul. 6, 2017 by Live-Pure, Inc. and Greg Sancoff et al. for SYSTEM FOR ASSESSING THE QUALITY OF AIR AND DRINKING WATER; and (ii) U.S. Provisional Patent Application Ser. No. 62/633,241, filed Feb. 21, 2018 by Live-Pure, Inc. and Greg Sancoff et al. for SYSTEM FOR ASSESSING THE QUALITY OF AIR AND DRINKING WATER.

The two (2) above-identified patent applications are hereby incorporated herein by reference.

FIELD OF THE INVENTION

This invention relates to home environmental test kits in general, and more particularly to systems for assessing the quality of air and drinking water.

BACKGROUND OF THE INVENTION

Consumers in the U.S. spend approximately $1.8 billion annually for air and water testing. Consumers in the U.S. also spend large amounts of money for air and water filtering.

By way of example, sales of freestanding air filtering systems are expected to surpass $85 million annually and to increase 17% through the year 2020 as consumers seek to ensure that the air they breathe in their home is clean. Additionally, $20.7 billion is spent annually on healthcare costs relating to breathing problems in the U.S. Consumers also spend large amounts of money on water filtering systems as consumers seek to ensure that the water they drink is clean and healthy.

In order to help consumers determine whether they live in a clean and safe environment, individual environmental test kits have been developed in order to test for contaminants identified by the Environmental Protection Agency (EPA) as having immediate and/or long term effects on the health and comfort of an individual, e.g., radon, mold and allergens, asbestos, lead, volatile organic compounds (VOCs), formaldehyde, water contaminants, etc.

Most environmental test kits require sophisticated training to use and are designed for use by professionals.

Some environmental test kits are designed for "home" use by a consumer. These "home" environmental test kits are generally designed to enable a consumer to perform a single environmental test, i.e., there is an individual test kit to test for a contaminant in water (e.g., lead), a different environmental test kit to test for a contaminant in air (e.g., asbestos), etc. Thus, a consumer must purchase multiple test kits in order to test for multiple environmental contaminants. Alternatively, some "home" environmental test kits exist which are able to test for multiple contaminants, but these test kits require that the consumer spend a significant amount of time and effort manually changing settings and/or parts for the test kit according to the particular test that is to be performed. Failure to change settings and/or parts correctly for each test generally results in unreliable test results.

Thus there is a need for an all-in-one, do-it-yourself environmental test kit which performs multiple environmental tests and which is adapted for easy use, and which provides higher quality testing and more accurate results.

SUMMARY OF THE INVENTION

The present invention comprises the provision and use of a novel system for assessing the quality of air and drinking water.

More particularly, the novel system comprises an all-in-one, do-it-yourself environmental test kit that is able to perform multiple environmental tests and which is adapted for easy use, and which provides higher quality testing and more accurate results.

In one form of the invention, there is provided a system for assessing the quality of air and/or drinking water, said system comprising:

a plurality of sample traps, wherein each of said sample traps is configured to test for a different environmental contaminant, and further wherein at least some of said sample traps require air to be drawn through that sample trap at a particular rate, and for a particular time duration, in order to properly test for a particular environmental contaminant;

a base unit, said base unit comprising:
  a pump for drawing air;
  a mount for connecting a sample trap to said pump so as to draw air through that sample trap when said pump is operated;
  a central processing unit (CPU) pre-programmed to operate said pump in a plurality of modes of operation, wherein each mode of operation causes said pump to draw air at a particular pump rate, and for a particular pump time duration; and
  a plurality of buttons communicating with said CPU, wherein activating a particular button causes said CPU to operate said pump in a particular mode of operation; and
  a marking scheme comprising a plurality of unique markings, wherein each of said buttons is marked with a different unique marking, and further wherein each of said at least some of said sample traps is marked with the same unique marking as the button which causes said pump to operate in the particular mode of operation required to draw air through that sample trap at the particular rate, and for the particular time duration, required for that sample trap to properly test for a particular environmental contaminant.

In another form of the invention, there is provided a method for assessing the quality of air and/or drinking water, the method comprising:

providing a system, said system comprising:
  a plurality of sample traps, wherein each of said sample traps is configured to test for a different environmental contaminant, and further wherein at least some of said sample traps require air to be drawn through that sample trap at a particular rate, and for a particular time duration, in order to properly test for a particular environmental contaminant;
  a base unit, said base unit comprising:
    a pump for drawing air;
    a mount for connecting a sample trap to said pump so as to draw air through that sample trap when said pump is operated;
    a central processing unit (CPU) pre-programmed to operate said pump in a plurality of modes of operation, wherein each mode of operation causes said pump to draw air at a particular pump rate, and for a particular pump time duration; and a plurality of buttons communicating with said CPU, wherein activating a particular button causes said CPU to operate said pump in a particular mode of operation; and a marking scheme comprising a plurality of unique markings, wherein each of said buttons is marked with a different unique marking, and further wherein each of said at least some of said sample traps is marked with the same unique marking as the button which causes said pump to operate in the particular mode of operation required to draw air through that sample trap at the particular rate, and for the particular time duration, required for that sample trap to properly test for a particular environmental contaminant;

mounting a sample trap to said pump; and activating the button having the same unique marking as the sample trap mounted to said pump.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 2 is a schematic view showing an exemplary list of the contents contained in the novel system shown in FIG. 1;

FIGS. 4-10 are schematic views showing details of the base unit of the novel system shown in FIG. 1;

FIGS. 24-32 are schematic views showing an exemplary use of the novel system shown in FIG. 1 for testing for environmental contaminants;

FIGS. 34-42 are schematic views showing details of an alternative adapter formed in accordance with the present invention.

DETAILED DESCRIPTION OF THE PREFERRED EMBODIMENTS

The present invention comprises the provision and use of a novel system for assessing the quality of air and drinking water.

More particularly, the novel system comprises an all-in-one, do-it-yourself environmental test kit which is able to perform multiple environmental tests and which is adapted for easy use, and which provides higher quality testing and more accurate results.

1. The System in General

Figure 1:
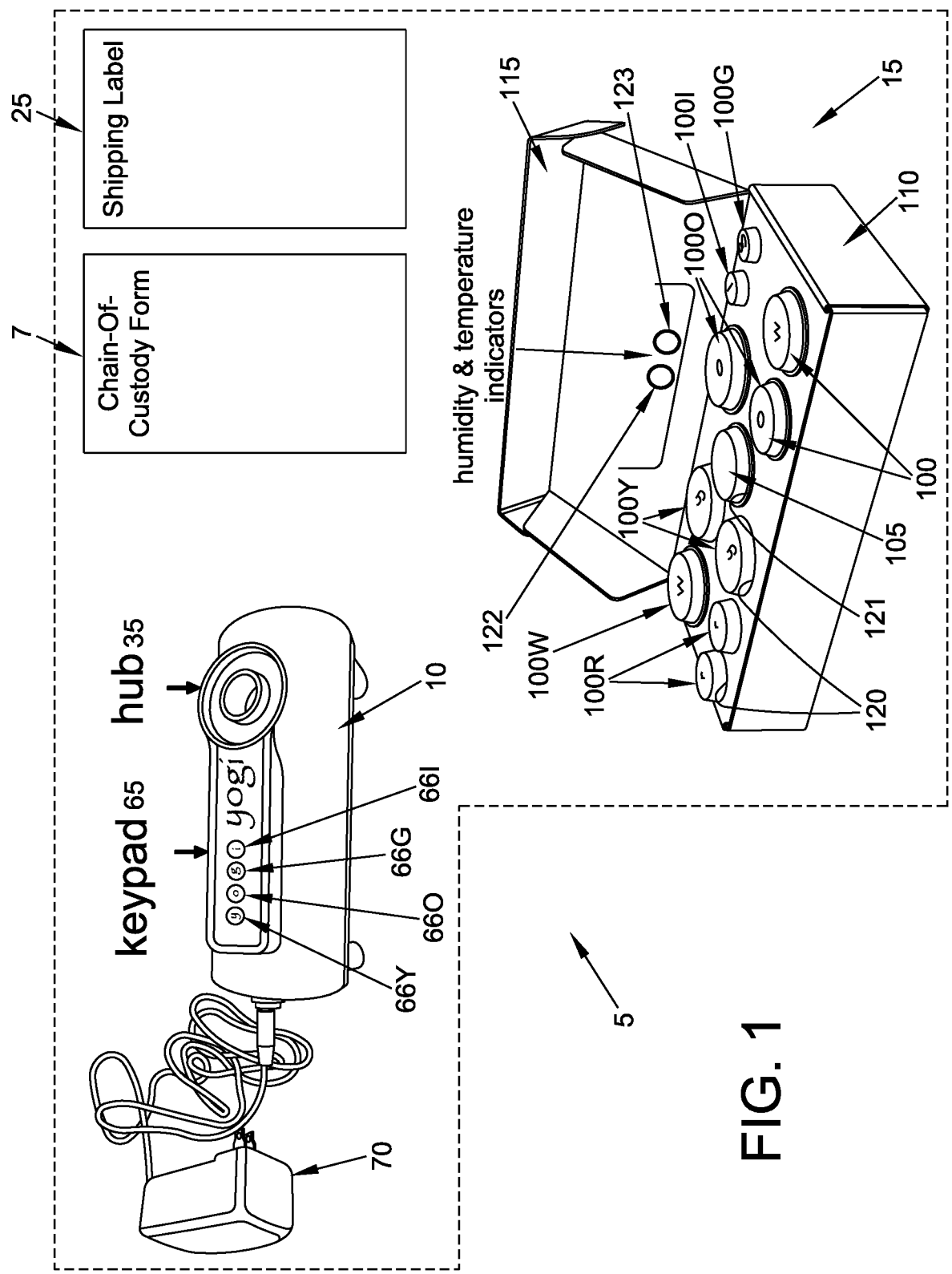
FIG. 1 is a schematic view showing a novel system for assessing the quality of air and drinking water.
Figure 3:
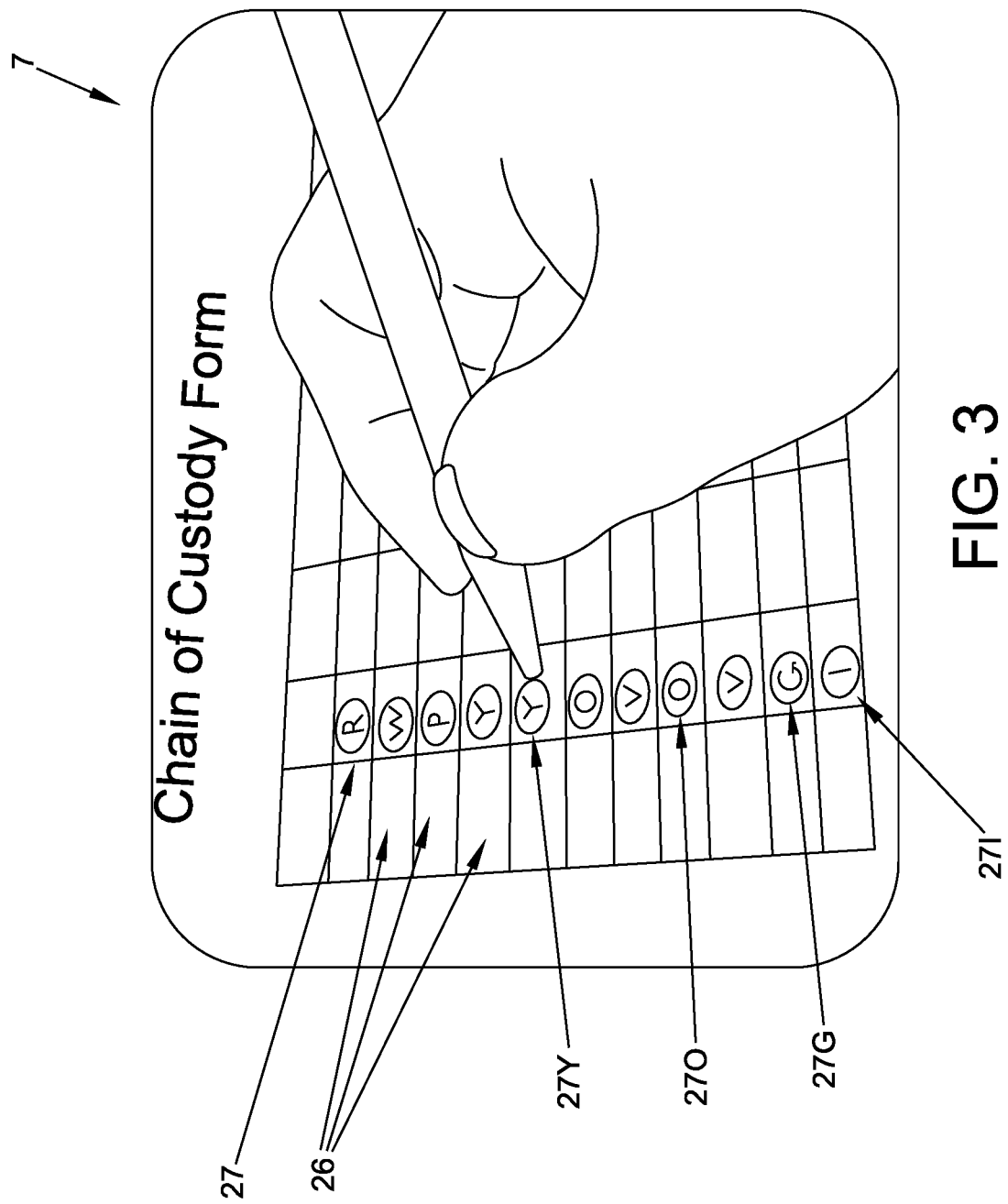
FIG. 3 is a schematic view showing an exemplary chain-of-custody form contained in the novel system shown in FIG. 1.
Figure 9:
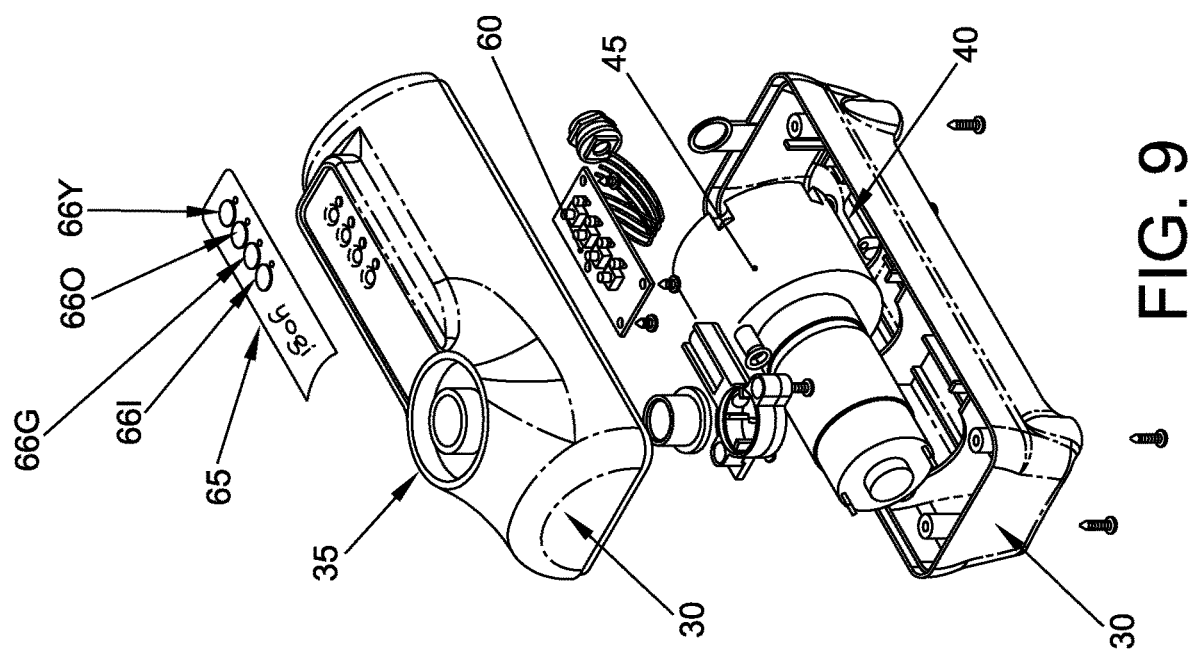
Figure 10:
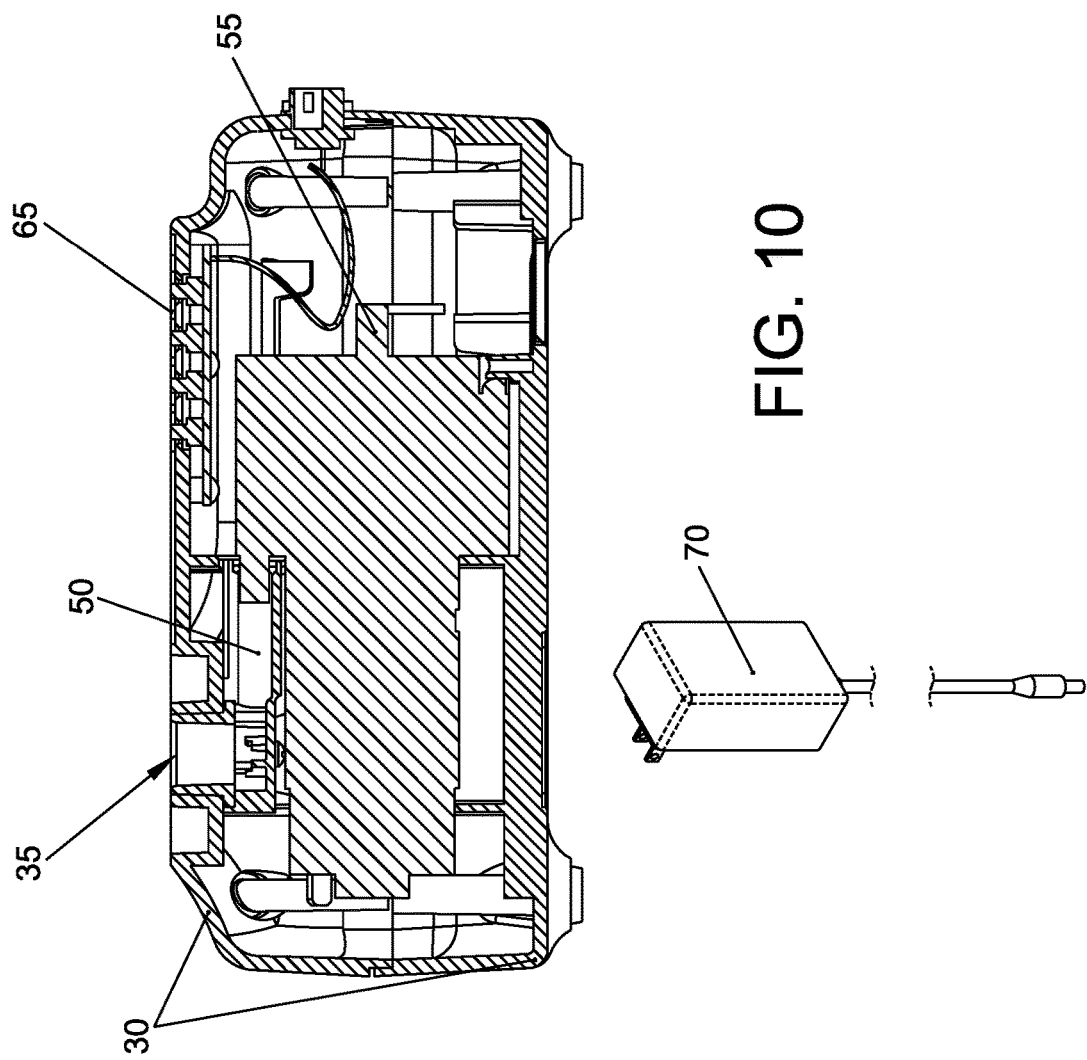

In one preferred form of the invention, and looking first at FIGS. 1-3, there is shown a novel system 5 for assessing the quality of air and drinking water. System 5 generally comprises a chain-of-custody form 7, a base unit 10, a sample box 15, and a shipping label 25, wherein base unit 10 and the capsules contained in sample box 15 (see below) are configured to, among other things, collect samples for environmental testing.

2. The Chain-of-Custody Form

In one preferred form of the invention, chain-of-custody form 7 contains a series of check-boxes 26 (FIG. 3) to be filled in by a consumer as they conduct various tests, and a plurality of circles 27 (FIG. 3) disposed adjacent to check-boxes 26, wherein each check-box 26 and each circle 27 corresponds to a specific environmental test which is to be run using a capsule contained in sample box 15. And in one preferred form of the invention, each circle 27 on chain-of-custody form 7 also comprises color-coding and/or letter-coding (see below) correlating to specific environmental tests, and to the capsules (see below) used in those tests, and to the specific operating modes of the motor (see below) of the pump (see below) of base unit 10 used in those tests. In one preferred form of the invention, the plurality of circles 27 comprise one or more yellow-coded and/or "Y"-coded circles 27Y, one or more orange-coded and/or "O"-coded circles 27O, one or more green-coded and/or "G"-coded circles 27G, and one or more indigo-colored and/or "I"-coded circles 27I.

By way of example but not limitation, in accordance with the present invention, a consumer proceeds down the list of tests on chain-of-custody form 7, performing the specific environmental tests desired, with those environmental tests being performed in the order in which the tests are listed on chain-of-custody form 7, and with the color-coding and/or letter-coding in circles 27 on chain-of-custody form 7 guiding which capsule is to be used for which test, and with the color-coding and/or letter-coding on chain-of-custody form 7 and on a specific capsule (see below) guiding the consumer's operation of base unit 10 for a specific test, by linking to a color-coded and/or letter-coded keypad (see below) which corresponds to various modes of operation for base unit 10, as will hereinafter be discussed in further detail. As each test is completed, the associated check-box 26 is marked to signify completion of that test.

It should be appreciated that chain-of-custody form 7 is configured to list the environmental tests in the order in which they are intended to be completed by a consumer and, thus, the order in which the environmental tests are intended to be run on base unit 10. It should be noted that if multiple tests are to be run using base unit 10, the tests requiring the highest pump speed (or, optionally, the longest pump run time) are completed first so as to warm up the pump contained in base unit 10 (see below), i.e., those tests will be listed ahead of other tests on chain-of-custody form 7, and the tests requiring the slowest pump speed (or, optionally, the shortest pump run time) are run last so as to ensure that the pump is properly warmed up when those tests are run, i.e., those tests will be listed at the end of chain-of-custody form 7.

In other words, chain-of-custody form 7 can be used to drive the use of system 5 by a consumer. More particularly, system 5 may comprise multiple environmental tests requiring different sampling procedures, but a consumer simply needs to follow the color-coded and/or letter-coded chain-of-custody form 7 in order to run the tests properly, i.e., the consumer does not require knowledge of the various sampling procedures in order to perform successful sampling which in turn leads to high quality and accurate test results. By way of example but not limitation, a consumer proceeds down the list of tests on chain-of-custody form 7, performing the specific environmental tests desired, with those environmental tests being performed in the order in which the tests are listed on chain-of-custody form 7, and with the color-coding and/or letter-coding on chain-of-custody form 7 (i.e., on the plurality of circles 27) guiding which color-coded and/or letter-coded capsule (see below) is to be used for which test, and with the color-coding and/or letter coding on chain-of-custody form 7 (and on a specific capsule) guiding the consumer's operation of base unit 10 for a specific test, i.e., by linking to a color-coded and/or letter-coded user interface keypad (see below) which corresponds to various modes of operation for base unit 10.

3. The Base Unit

Base unit 10 is shown in detail in FIGS. 4-11. Base unit 10 generally comprises a housing 30, an air input 35, an air output 40, a pump 45, an input air line 50, an output air line 55, a CPU 60, a user interface 65 comprising a plurality of color-coded and/or letter-coded buttons 66 (e.g., a yellow-coded and/or "Y"-coded button 66Y, an orange-coded and/or "O"-coded button 66O, a green-coded and/or "G"-coded button 66G, and an indigo-coded and/or "I"-coded button 66I) and a power supply 70.

In one form of the invention, base unit 10 may also comprise a dust cover (not shown) for protecting air input 35 from contaminants when base unit 10 is not in use.

3.1 Housing 30

As seen in FIGS. 4-10, housing 30 is configured to support air input 35 and air output 40, and the interior of housing 30 is configured to hold pump 45, input air line 50, output air line 55 and CPU 60.

3.2 Air Input 35

Figure 11:
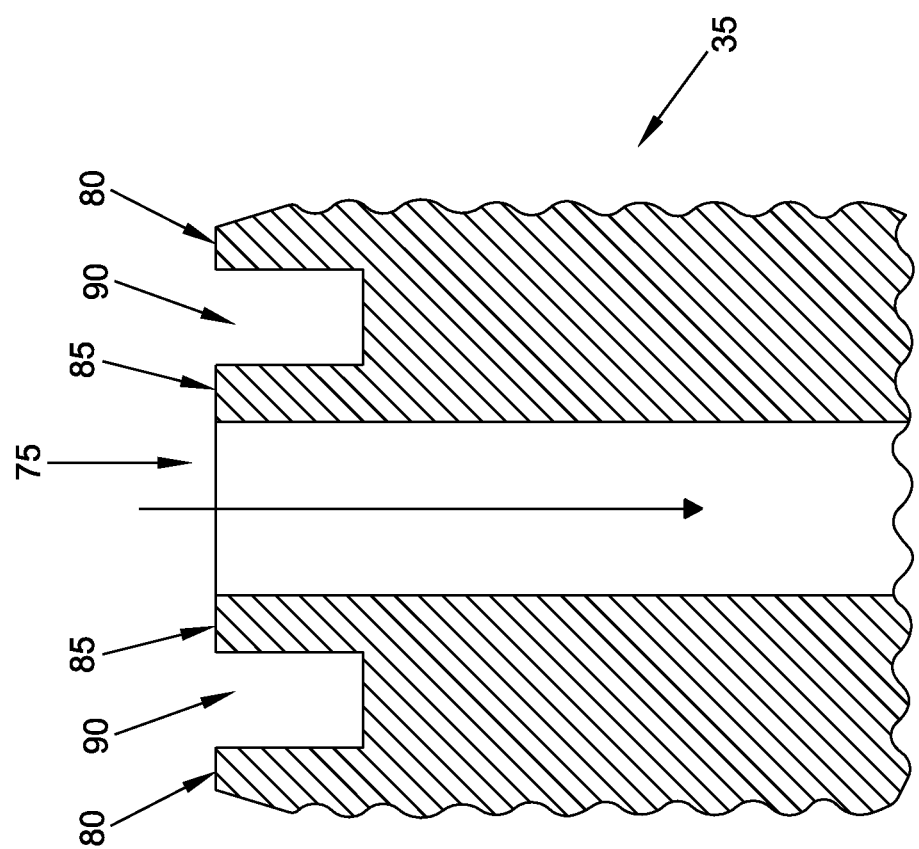
FIG. 11 is a schematic view showing details of the air input of the base unit shown in FIGS. 4-10.

Air input 35 is configured to allow a sample trap (see below) to be attached to housing 30 and for air to be drawn through the sample trap (see below). As seen in FIG. 11, air input 35 generally comprises an opening 75, an outer rim 80, an inner rim 85, and a recess 90 disposed between outer rim 80 and inner rim 85. In one preferred form of the invention, outer rim 80 comprises a "key" protrusion 92 (FIG. 16) for connection with a counterpart "key" notch on a sample trap, as will hereinafter be discussed in further detail.

3.3 Air Output 40

Air output 40 is configured to allow air from pump 45 to exit housing 30.

3.4 Pump 45

Pump 45 preferably comprises a diaphragm pump (sometimes also referred to as a positive displacement pump) which provides variable pumping rates with high accuracy. More particularly, a diaphragm pump (i.e., a positive displacement pump) works by advancing a fixed volume of material through the pump, and thus the volume of material being advanced through the pump is constant through each cycle of operation, thereby allowing a precision flow rate at a given speed and hence high pump accuracy. This is in contrast to the blowers or fans used in currently available "home" environmental test kits.

In one preferred form of the invention, pump 45 comprises pump model AJK-B12A3601 available from Xiamen AJK Technology Co., Ltd. of 256-260 HuanZhu Road, JiMei zone, Xiamen City, Fujian Provence, China.

3.5 Input Air Line 50

Input air line 50 is disposed between air input 35 and pump 45 and is configured to pass air from air input 35 into pump 45.

3.6 Output Air Line 55

Output air line 55 is disposed between pump 45 and air output 40 and is configured to pass air from pump 45 into the environment outside of base unit 10.

3.7 CPU 60

CPU 60 is disposed in housing 30. CPU 60 is programed to operate pump 45 according to the particular button 66 pressed on user interface 65, e.g., when the yellow "Y" button 66Y on user interface 65 is pressed, CPU 60 causes pump 45 to run for a duration of 5 minutes at a rate of 15 liters per minute (LPM); when the orange "O" button 66O on user interface 65 is pressed, CPU 60 causes pump 45 to run for a duration of 15 minutes at a rate of 5 LPM; when the green "G" button 66G on user interface 65 is pressed, CPU 60 causes pump 45 to run for a duration of 7 minutes at a rate of 0.2 LPM; and when the indigo "I" button 66I on user interface 65 is pressed, CPU 60 causes pump 45 to run for a duration of 2 hours at a rate of 0.2 LPM, etc.

Significantly, and as will hereinafter be discussed, by correlating a particular button 66 on user interface 65 with the pump requirements associated with a particular test (i.e., via color-coding and/or letter-coding), CPU 60 can run pump 45 in the manner which is appropriate for each specific test which is to be run. In one form of the present invention, CPU 60 stores the modes of operation (i.e., the pump parameters) in non-volatile memory, e.g., EEPROM.

CPU 60 is configured to adjust the voltage supplied to pump 45, and to adjust the duration of the voltage applied to pump 45, so as to achieve the desired pump operation for a particular test. In other words, a particular test generally requires a particular pump flow rate, and a particular duration of pumping, and CPU 60 causes pump 45 to provide the desired pump flow rate, and the desired duration of pumping, by regulating the voltage powering pump 45.

Figure 12:
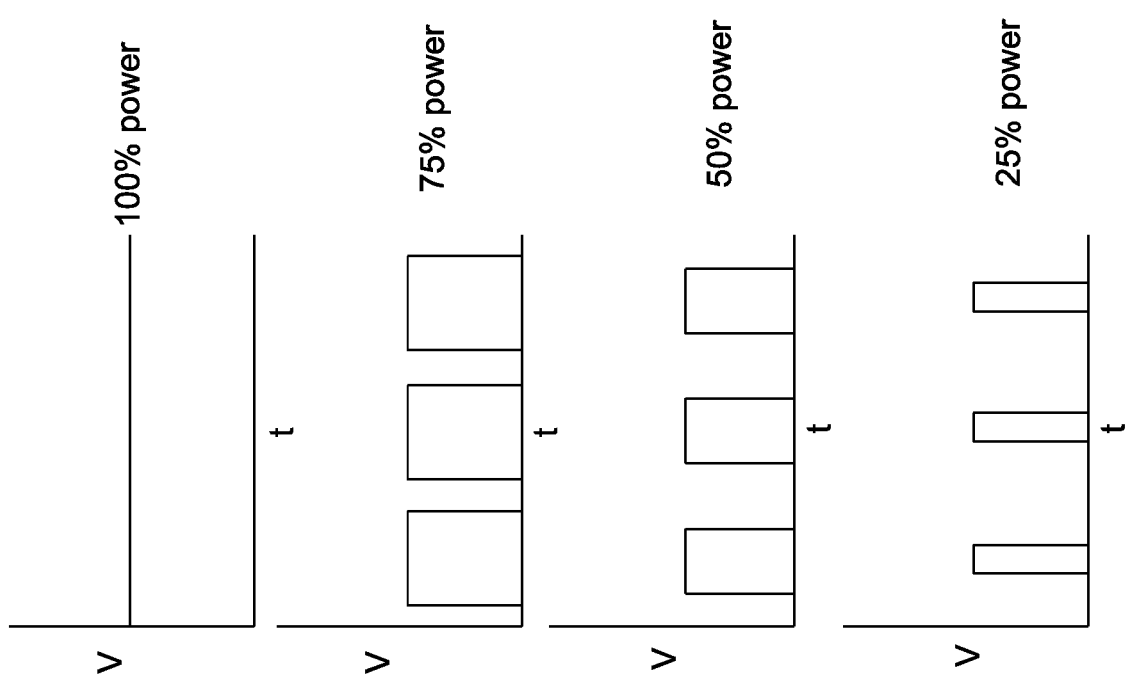
FIG. 12 is a schematic view showing how pulse width modulation (PWM) may be used to provide various levels of power to the motor of a pump contained within the base unit shown in FIGS. 4-10.

In one preferred form of the invention, the voltage delivered to pump 45 comprises pulse width modulated (PWM) digital signals which allow for precise control of the speed and duration of the operation of pump 45. With PWM operation, CPU 60 sends wider, more tightly packed pulses for greater pump power, and CPU 60 sends thinner, less tightly packed pulses for lower pump power. The pulses are averaged, and the result is a nominal DC voltage value between 0-12 VDC for 0%-100% pump power. See, for example, FIG. 12, which shows pulse width modulation for providing various levels of pump power.

Significantly, pulse width modulation also allows for precise calibration of pump 45, which is important inasmuch as pump 45 must provide highly accurate pumping action in order for system 5 to achieve highly accurate/high quality test results.

Therefore, in one preferred form of the invention, CPU 60 may also comprise a calibration mode of operation for calibrating pump 45. In this respect it should be appreciated that the pump 45 contained in every base unit 10 is calibrated before being sent to a consumer in order to ensure highly accurate pump performance. This is important, because each motor used to drive pumps 45 has varying performance characteristics (i.e., different motor efficiency for the same voltage input). This is typically due to inconsistencies in motor windings and brushes. The calibration mode for CPU 60 allows the operation of each motor to be adjusted as needed in order to achieve precise pump performance characteristics.

Figure 13:
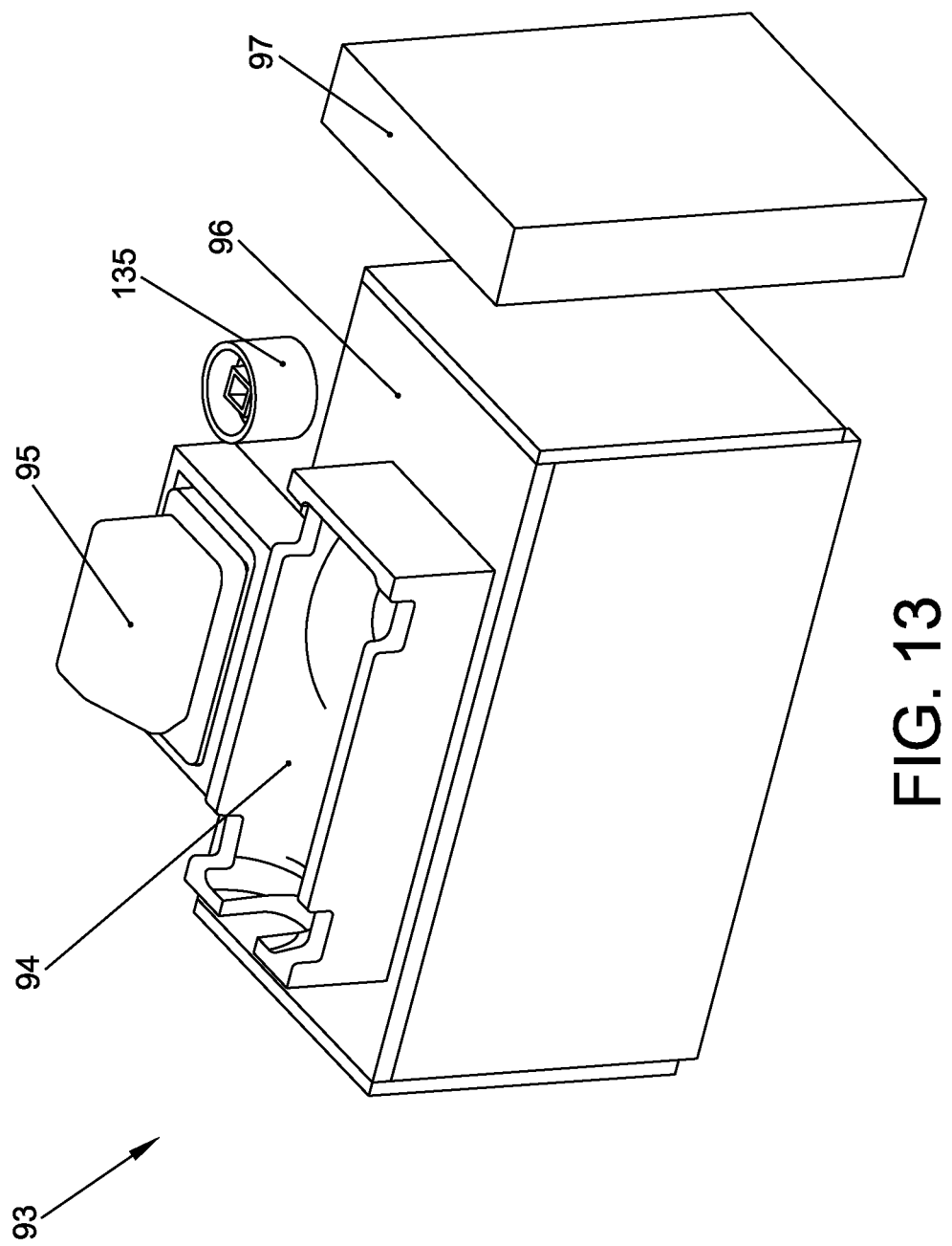
FIG. 13 is a schematic view showing a calibration fixture which may be used to calibrate the motor of a pump contained within the base unit shown in FIGS. 4-10.

In one form of the invention, and looking now at FIG. 13, each pump 45 is preferably calibrated as follows.

(i) A calibration fixture 93 is provided. Calibration fixture 93 comprises a unit carrier 94, a flow meter 95, a calibration stand 96 and calibration electronics 97 (which control the operation of the pump which is being calibrated). Sample traps are used to carry out the environmental tests. Note that different environmental tests require different sample traps, and each sample trap may require a different flow rate and/or a different flow time. It is important that the motor driving the pump be capable of providing, with precision, the specific flow rates and the specific flow times required for each sample trap. To this end, each pump 45 is calibrated for each type of sample trap, with the calibration equipment checking motor performance against the specific air flow requirements, and the specific flow time requirements, for each type of sample trap, and modifying the motor parameters as necessary if the pump performance is outside a sample trap's specifications. A calibration program controls calibration electronics 97 and calibrates each pump for each of the flow rates, and for each of the flow times, required for each type of sample trap. Thus, for example, where a pump should run at 15 liters per minute (LPM) for 5 minutes for a certain sample trap, 5 LPM for 15 minutes for another type of sample trap, 0.2 LPM for 20 minutes for still another type of sample trap, and 0.2 LPM for 2 hours for yet another type of sample trap, each pump is calibrated for each of these flow rates, and for each of these flow times, while the appropriate sample trap is attached to the pump.

(ii) For each type of sample trap and its associated target flow rates (and target flow times), the appropriate sample trap is attached to calibration fixture 93 and the calibration program energizes the motor driving the pump according to the manufacturer's instructions for the desired flow rate, and then the calibration fixture reads the actual flow rate from the output of flow meter 95. If the flow rate does not fall within previously-set upper and lower flow rate limits, the calibration program adjusts the motor speed of the pump so as to achieve the intended flow rate and then re-writes this actual motor speed to the printed circuit board (PCB) for the pump.

(iii) The calibration program will do incremental adjustments to the motor speed for the pump until the flow rate of the pump is within the previously-set upper and lower flow rate limits. Once the flow rate is within the previously-set upper and lower flow rate limits, the calibration program does a final write to the PCB for the pump.

3.8 User Interface 65

Figure 14:
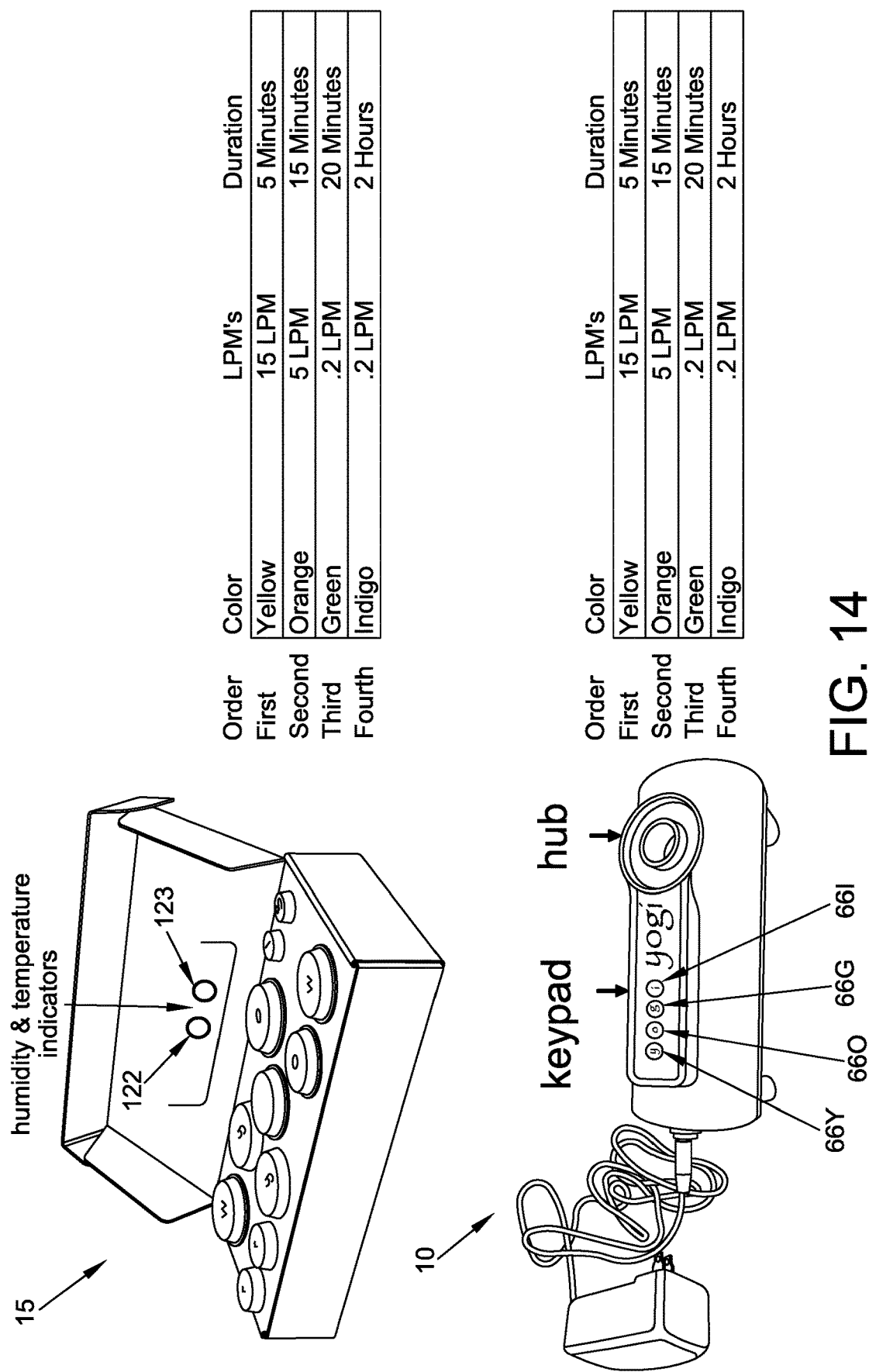
FIG. 14 is a schematic view showing how the novel system of FIG. 1 may be used for testing environmental contaminants.

As seen in FIG. 14, user interface 65 of base unit 10 comprises a color-coded and/or letter-coded keypad comprising a plurality of color-coded and/or letter-coded buttons 66 (e.g., a yellow-coded and/or "Y"-coded button 66Y, an orange-coded and/or "O"-coded button 66O, a green-coded and/or "G"-coded button 66G, and/or an indigo-coded and/or "I"-coded button 66I), each of which corresponds to a particular mode of operation for pump 45 (i.e., a specific pump speed and pumping duration for one mode, another specific pump speed and pumping duration for another mode, etc.). Note that the color-coding and/or letter-coding of each button 66 on user interface 65 also correlates to corresponding color-coding and/or letter-coding on the capsules contained in sample box 15 (which will be discussed in further detail below), and color-coding and/or letter-coding on chain-of-custody form 7 (e.g., the orange "O" button 66O on user interface 65 corresponds to an orange "O" capsule in sample box 15 and an orange "O" circle 27O on chain-of-custody form 7, the yellow "Y" button 66Y on user interface 65 corresponds to a yellow "Y" capsule in sample box 15 and a yellow "Y" circle 27Y on chain-of-custody form 7, etc.). It will be appreciated that the aforementioned color-coding and/or letter-coding embedded in system 5 allows for easy use of the various components of system 5 by a consumer.

In one preferred form of the invention, user interface 65 comprises the aforementioned 4 color-coded and/or letter coded buttons 66, i.e., the yellow "Y" button 66Y, the orange "O" button 66O, the green "G" button 66G and the indigo "I" button 66I, wherein each button 66 corresponds to a specific mode of operation for pump 45. More particularly, in one preferred form of the invention, and looking still at FIG. 14, pressing the yellow "Y" button 66Y runs pump 45 for a duration of 5 minutes at 15 liters per minute (LPM), pressing the orange "O" button 66O runs pump 45 for a duration of 15 minutes at 5 LPM, pressing the green "G" button 66G runs pump 45 for a duration of 20 minutes at 0.2 LPM, and pressing the indigo "I" button 66I runs pump 45 for a duration of 2 hours at 0.2 LPM.

3.9 Power Supply 70

Power supply 70 preferably comprises a 12 volt power supply and is provided separately from base unit 10. It will be appreciated that power supply 70 may also be configured to fit inside housing 30 of base unit 10 if desired, e.g., where power supply 70 comprises a battery.

4. The Sample Box and its Capsules

Figure 15:
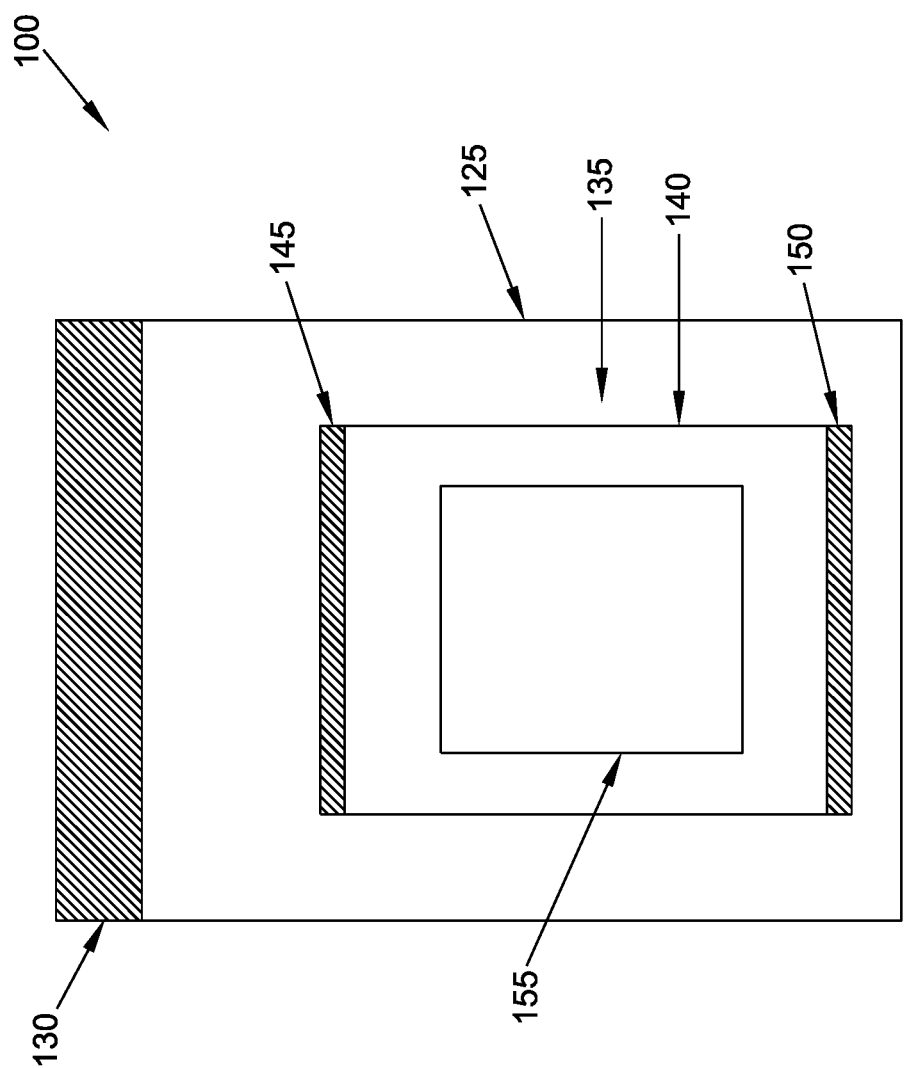
FIG. 15 is a schematic view showing details of an exemplary capsule (which may also be referred to as a container or canister) of the novel system shown in FIG. 1.

Looking now at FIGS. 1 and 15, sample box 15 generally contains a plurality of capsules 100 (e.g., one or more yellow-coded and/or "Y"-coded capsules 100Y, one or more orange-coded and/or "O"-coded capsules 100O, one or more green-coded and/or "G"-coded capsules 100G, one or more indigo-coded and/or "I"-coded capsules 100I, etc.), and one or more adapters 105.

4.1 Sample Box 15

Sample box 15 (FIG. 1) generally comprises a body 110, a lid 115, a plurality of recesses 120 for receiving capsules 100, and a plurality of recesses 121 for receiving adapters 105. Each capsule 100 corresponds to a different type of environmental test, e.g., a test for radon, a test for contaminants in water, a test for contaminants in outside air, a test for contaminants in inside air, a test for asbestos, a test for lead, a test for formaldehyde, a test for volatile organic compounds (VOCs), etc.

In one preferred form of the invention, lid 115 of sample box 15 comprises a humidity indicator 122 and a temperature indicator 123 so as to provide a consumer with humidity and temperature information of the environment in which a specific test is performed. It should be appreciated that the humidity and temperature of a location during testing may be important for accurate results and therefore sections may be included in chain-of-custody form 7 to provide this information to the testing laboratory.

4.2 Capsules 100

Capsules 100 (FIG. 15) generally comprise a body 125, a cap 130 and a sample trap 135. In one preferred form of the invention, cap 130 of capsule 100 is color-coded and/or letter-coded to match a color-coded and/or letter-coded circle 27 on chain-of-custody form 7 and, for those tests that require the use of base unit 10, the color-coding and/or letter-coding of cap 130 also corresponds to the color-coding and/or letter-coding on user interface 65 of base unit 10 (e.g., a color-coded and/or letter-coded button 66). By way of example but not limitation, a test for contaminants in air may be contained in a capsule 100Y with a yellow "Y" cap 130, which corresponds to a test on chain-of-custody form 7 marked with a yellow "Y" circle 27Y and which corresponds to a yellow "Y" button 66Y on user interface 65 of base unit 10. It will be appreciated that body 125 of capsule 100 may also be color-coded and/or letter-coded in conjunction with cap 130.

Figure 16:
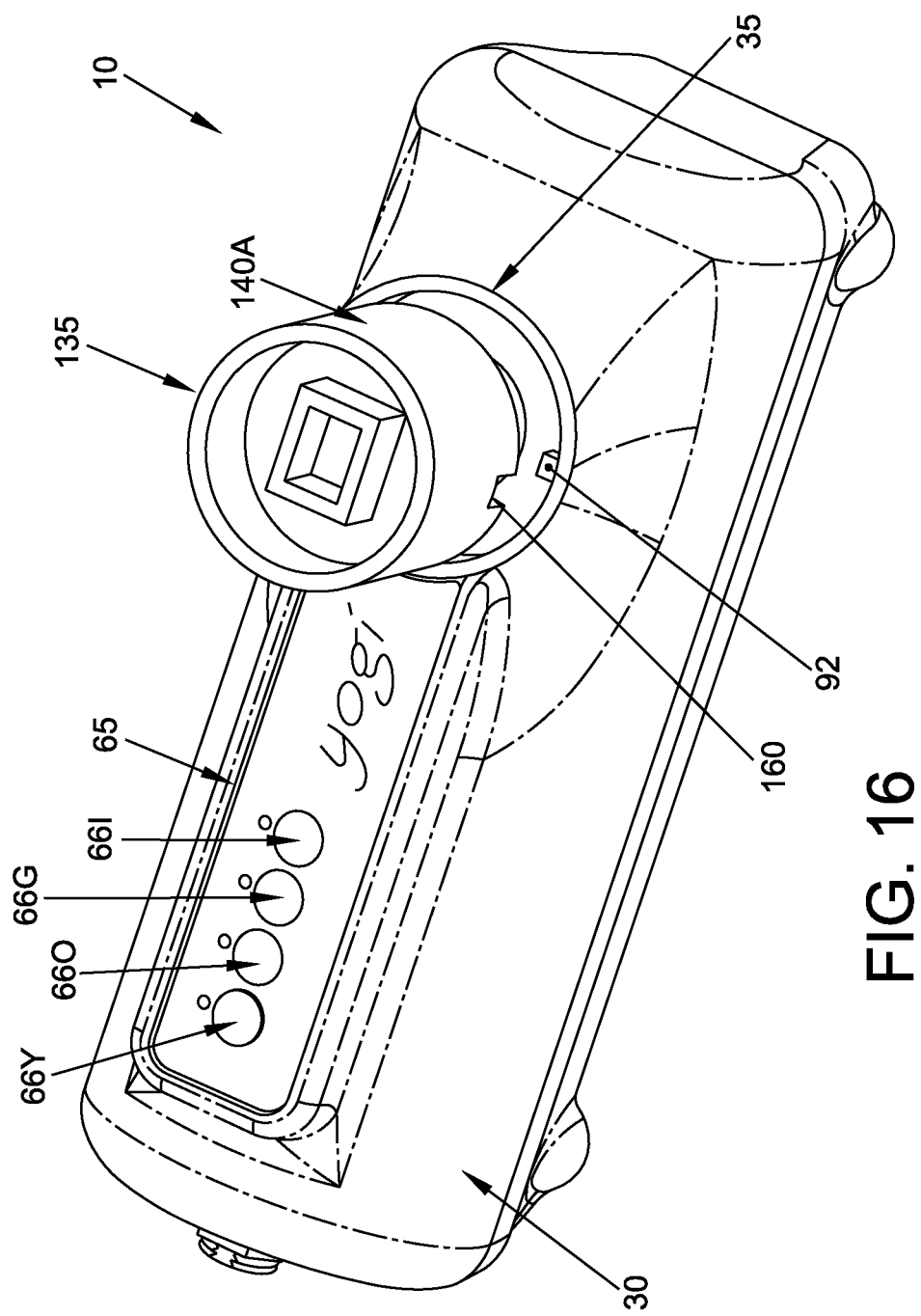
FIGS. 16 and 17 are schematic views showing the connection of one type of sample trap with the air input of the base unit of the novel system shown in FIG. 1.

Still looking at FIG. 15, sample trap 135 of capsule 100 generally comprises a body 140, a top seal 145, a bottom seal 150, trap material 155 and a "key" notch 160 (FIG. 16) for connection with "key" protrusion 92 of outer rim 80 of air input 35 of base unit 10, wherein key notch 160 is configured to "lock" sample trap 135 in place on air input 35 of base unit 10 via key protrusion 92 (see FIG. 16).

In one preferred form of the invention, sample traps 135 are provided in sample box 15 for the following environmental tests: a test for radon in air; a test for contaminants in water; a test for contaminants in outside air; a test for contaminants in inside air; a test for asbestos in air; a test for lead in air; a test for formaldehyde in air; and a test for volatile organic compounds (VOCs) in air. In the aforementioned preferred form of the invention, sample traps 135 of capsules 100 comprise radon traps; water vial or small bottle traps; spore traps; fiber traps; dust traps; and glass tube traps.

Figure 17:
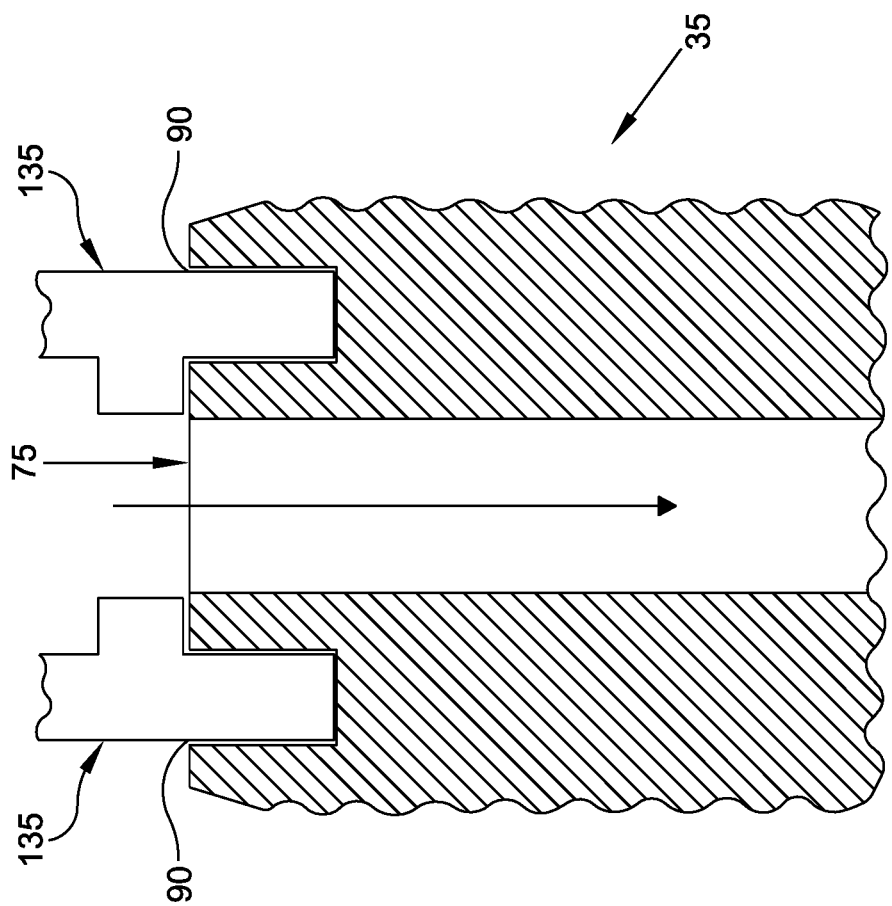
Figure 21:
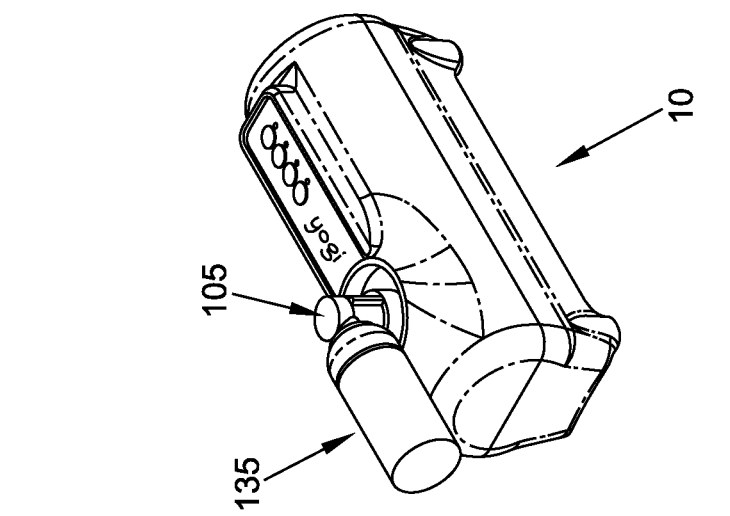
FIGS. 18-23 are schematic views showing how various adapters may be used to connect a sample trap to the air input of a base unit.
Figure 20:
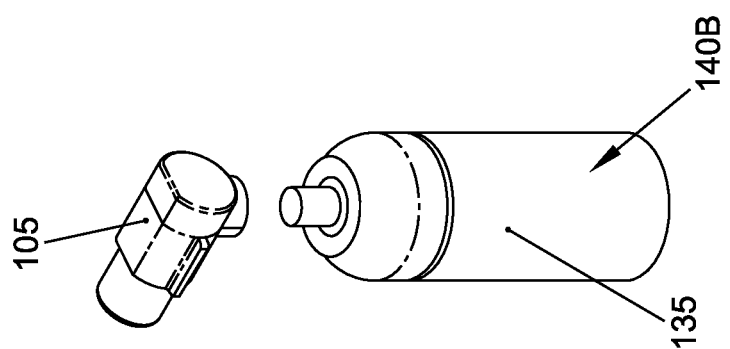
Figure 18:
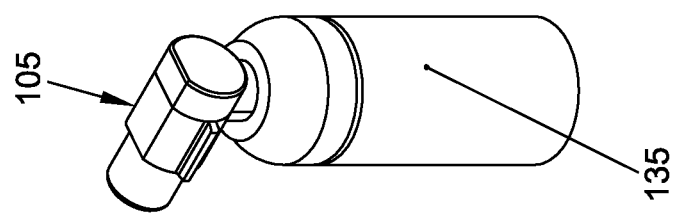
Figure 19:
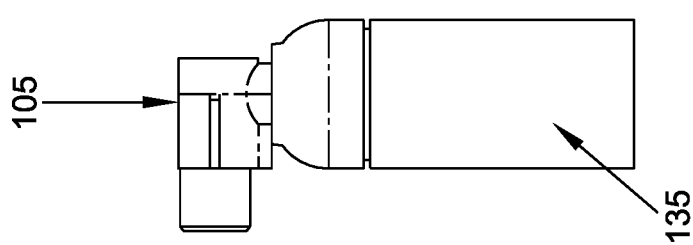

It will be appreciated that body 140 of sample trap 135 is intended to be mounted to air input 35 of base unit 10, such that base unit 10 can be used to draw air through body 140 of sample trap 135 and thereby trap a particular contaminant in the trap material 155 of that sample trap. It will be appreciated that, to this end, body 140 of sample trap 135 is generally configured to fit between outer rim 80 and inner rim 85 (i.e., in recess 90) of air input 35 of base unit 10. It will also be appreciated that if body 140 of sample trap 135 requires, for functional and/or other reasons, a configuration other than that which fits between outer rim 80 and inner rim 85 (i.e., in recess 90) of air input 35 of base unit 10, adapter 105 is used to connect sample trap 135 to base unit 10. See, for example, FIGS. 16 and 17 which show a sample trap mounting directly to air input 35 of base unit 10, and FIGS. 18-23, which show adapter 105 being used to mount a sample trap to air input 35 of base unit 10.

More particularly, where sample trap 135 is designed to test for mold, it may comprise a body 140A (FIGS. 16 and 17) which seats directly on air input 35 of base unit 10, without requiring an adapter 105; where sample trap 135 is designed to test for asbestos in the air, it may comprise a body 140B (FIGS. 18-21) which utilizes an adapter 105 to seat on air input 35 of base unit 10; where sample trap 135 is designed to test for lead, it may comprise a body 140C (FIG. 22) which also utilizes an adapter 105 to seat on air input 35 of base unit 10; and where sample trap 135 is designed to test for VOCs and/or formaldehyde, it may comprise a body 140D (FIG. 23) which also utilizes an adapter 105 to seat on air input 35 of base unit 10.

In one form of the invention, top seal 145 of sample trap 135 and bottom seal 150 of sample trap 135 comprise reusable adhesive cover seals which may be removed from sample trap 135 before use, and then used to re-seal sample trap 135 after sample trap 135 has collected a sample (see below). In another preferred form of the invention, top seal 145 and bottom seal 150 comprise plastic caps which mount onto body 140 of sample trap 135 (e.g., plastic caps which insert into body 140 of sample trap 135 or which fit over body 140 of sample trap 135). In yet another preferred form of the invention, top seal 145 and bottom seal 150 comprise stoppers. It will be appreciated that top seal 145 and bottom seal 150 may also comprise a combination of a reusable adhesive seal and a plastic cap, or a plastic cap and a stopper, etc.

Trap material 155 generally comprises the material necessary to trap contaminants for a particular environmental test, and/or a material to ensure stability of a contaminant sample once the contaminant has been captured in trap material 155. By way of example but not limitation, trap material 155 may comprise the materials necessary for a radon trap, water stabilizer(s), the materials necessary for a spore trap, the materials necessary for a dust trap, the materials necessary for a glass tube trap, etc. By way of further example but not limitation, where a sample trap 135 comprises a body 140A and is designed to test for mold, trap material 155 may comprise the materials necessary for a spore trap; where a sample trap 135 comprises a body 140B and is designed to test for asbestos, trap material 155 may comprise the materials necessary for trapping asbestos fibers; where a sample trap 135 comprises a body 140C and is designed to test for lead, trap material 155 may comprise the materials necessary for trapping dust carrying lead particles; and where a sample trap 135 comprises a body 140D and is designed to test for VOCs and/or formaldehyde, trap material 155 may comprise the materials necessary for trapping VOCs and/or formaldehyde. It will be appreciated that trap material 155 is not limited to the specific environmental tests discussed above, but may also be configured for a variety of other environmental tests for contaminants in air and water.

As discussed previously, adapters 105 are provided for those sample traps 135 which are not configured to mount directly to air input 35 of base unit 10, i.e., where a sample trap 135 does not fit between outer rim 80 and inner rim 85 (i.e., in recess 90) of air input 35 of base unit 10. In general, adapters 105 comprise one end which is configured to mate with air input 35 of base unit 10 by fitting between outer rim 80 and inner rim 85 (i.e., in recess 90) of air input 35 of base unit 10, and an opposing end which is configured to mate with a specific sample trap 135.

By way of example but not limitation, where a sample trap 135 is designed to test for mold and comprises a body 140A, body 140A is configured to mount directly to air input 35 of base unit 10 and no adapter 105 is needed; where a sample trap 135 is designed to test for asbestos and comprises a body 140B which is not configured to mount directly to air input 35 of base unit 10, an adapter 105 is used to mount body 140B to air input 35 of base unit 10; where a sample trap 135 is designed to test for lead and comprises a body 140C, an adapter 105 is used to mount body 140C to air input 35 of base unit 10; and where a sample trap 135 is designed to test for VOCs and/or formaldehyde and comprises a body 140D, an adapter 105 is used to mount body 140D to air input 35 of base unit 10.

Figure 23:
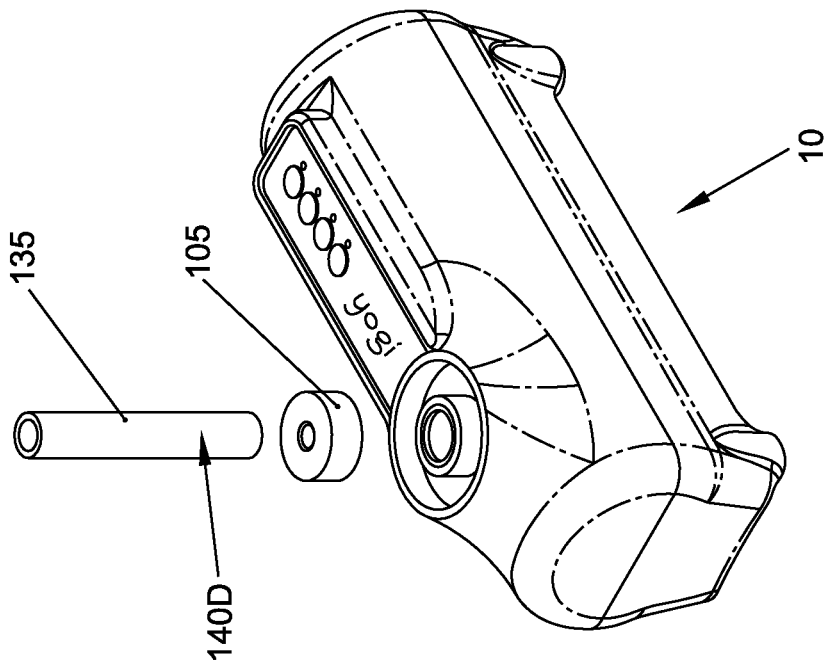
Figure 22:
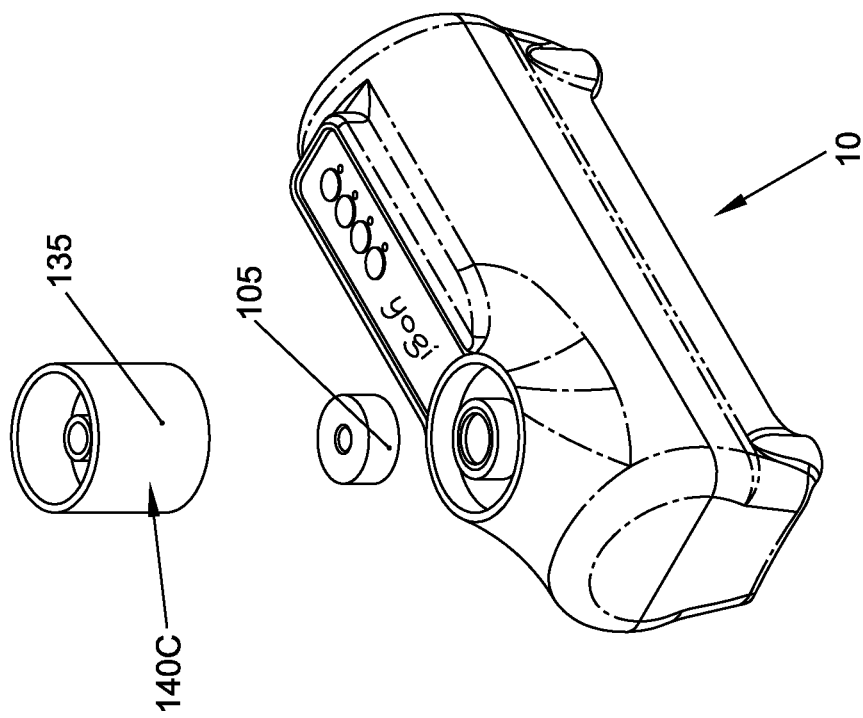

Note that the configuration of adapters 105 can vary according to the configuration of the body of the sample trap, e.g., in one form of the invention, adapters 105 comprise an elbow adapter (FIGS. 18-21); and in another form of the invention, adapters 105 comprise "straight line" adapters (FIGS. 22 and 23).

Note also that adapters 105 can be pre-mounted to a sample trap 135 if desired.

In one preferred form of the invention, sample box 15 comprises the following components:

(i) two red "R" capsules 100R comprising a test for radon in air, wherein sample trap 135 comprises a radon trap;

(ii) two white "W" capsules 100W comprising a test for contaminants in water, wherein sample trap 135 comprises a water vial or small bottle;

(iii) a yellow "Y" capsule 100Y comprising a test for outside air contaminants, wherein sample trap 135 comprises a spore trap;

(iv) a yellow "Y" capsule 100Y comprising a test for inside air contaminants, wherein sample trap 135 comprises a spore trap;

(v) an orange "O" capsule 100O comprising a test for asbestos in air, wherein sample trap 135 comprises a fiber trap and an adapter 105 pre-mounted to sample trap 135;

(vi) an orange "O" capsule 100O comprising a test for lead in air, wherein sample trap 135 comprises a dust trap;

(vii) a green "G" capsule 100G comprising a test for formaldehyde in air, wherein sample trap 135 comprises a glass tube trap;

(viii) an indigo "I" capsule 100I comprising a test for volatile organic compounds (VOCs) in air, wherein sample trap 135 comprises a glass tube trap;

(ix) an adapter 105 for use with an orange "O" capsule 100O comprising a test for lead in air, or a green "G" capsule 100G comprising a test for formaldehyde in air or an indigo "I" capsule 100I comprising a test for volatile organic compounds (VOCs) in air; and (x) a chain-of-custody form 7 comprising a check-box 26 and a color-coded and/or letter-coded circle 27 for each of the above-identified capsules 100.

It should be appreciated that the unifying color-coding and/or letter-coding theme incorporated in system 5 (i.e., the color-coding and/or letter-coding of chain-of-custody form 7, the color-coding and/or letter-coding of capsules 100, and the color-coding and/or letter-coding of user interface 65) allows a consumer to easily perform multiple environmental tests while still obtaining high quality and accurate tests results. More particularly, a consumer simply follows, in order, the top-to-bottom sequence of the circles 27 on chain-of-custody form 7, and each circle 27 on chain-of-custody form 7 is color-coded and/or letter-coded to a particular capsule 100 (i.e., a particular environmental test) and, where appropriate, is color-coded and/or letter-coded to a particular button 66 on user interface 65. The color-coded and/or letter-coded button 66 on user interface 65 corresponds to a specific mode of operation (i.e., to specific pump operational parameters) stored in CPU 60, with the color-coding and/or letter-coding ensuring that each environmental test is run under optimal pump conditions for collecting a particular sample. The appropriate check-box 26 corresponding to a color-coded and/or letter-coded circle 27 of chain-of-custody form 7 is filled out as each of the tests is run, with each sample trap 135 being re-sealed back within its associated capsule 100, and with each capsule 100 being replaced within sample box 15. Once all tests are complete, sample box 15 is sealed and sent to a certified laboratory for testing using shipping label 25.

5. Use of the System in General

Looking now at FIGS. 1, 14 and 24-32, system 5 is generally intended to be used as follows. Base unit 10 is prepared for use by plugging in power supply 70. Next, following the order of the tests on chain-of-custody form 7, a capsule 100 is selected for the test which is to be run, e.g., a test for radon, a test for mold and allergens, etc. Cap 130 is removed from capsule 100 and sample trap 135 is removed from capsule 100 (if necessary). If applicable, top seal 145 and bottom seal 150 are removed from sample trap 135, and sample trap 135 is mounted to air input 35 of base unit 10. If sample trap 135 has a configuration which matches the configuration of air input 35 of base unit 10, no adapter 105 needs to be positioned between sample trap 135 and air input 35 of base unit 10; if sample trap 135 has a configuration which is different than that of air input 35, then an adapter 105 is first placed on air input 35 of base unit 10, and then sample trap 135 is placed into adapter 105, whereby to mount sample trap 135 to air input 35 of base unit 10. Sample trap 135 is preferably locked into place using key protrusion 92 of outer rim 80 of air input 35 and key notch 160 of sample trap 135.

Once sample trap 135 is mounted to base unit 10, user interface 65 is used to appropriately operate pump 45, e.g., if cap 130 of capsule 100 is orange and/or has an "O", the orange and/or "O" button of user interface 65 is pressed and CPU 60 causes pump 45 to operate at the appropriate speed, and for the appropriate period of time, for the test associated with orange "O" capsule 100O. When pump 45 shuts off, base unit 10 will beep, signaling that sample trap 135 is ready to be removed from air input 35 of base unit 10. If adapter 105 is being used, sample trap 135 is removed from adapter 105, and adapter 105 is subsequently removed from base unit 10 (if necessary).

Next, if applicable, top seal 145 and bottom seal 150 are placed back onto sample trap 135 in order to seal the contents of sample trap 135, whereby to prevent decomposition/contamination of the air/water trapped in sample trap 135. Once re-sealed, sample trap 135 is placed back into capsule 100, cap 130 is placed back onto capsule 100, and capsule 100 is placed into a recess 120 of sample box 15.

After placement of capsule 100 into recess 120 of sample box 15, the corresponding check-box 26 is checked on chain-of-custody form 7, i.e., the check-box 26 corresponding to the appropriate color-coded and/or letter-coded circle 27 for the environmental test which was just run on base unit 10.

Additional tests may be run in the same manner as discussed above and the capsules 100 for those tests placed in sample box 15.

When all of the desired tests have been run, and capsules 100 re-seated in recesses 120 of sample box 15, chain-of-custody form 7 is placed in sample box 15 and sample box 15 is sealed for shipping. Note that adapter 105 should be removed from sample box 15 before sealing sample box 15. Shipping label 25 is then placed on the outside of sample box 15 and sample box 15 is shipped to a certified laboratory for testing. The consumer may receive results as soon as 4 days after the certified testing lab receives sample box 15. Results may be received by the consumer via E-mail.

5.1 Exemplary Use

The following discussion shows some exemplary uses of system 5 for testing environmental contaminants in air and water. It will be appreciated that the following discussion is provided by way of example only and in no way limits the present invention to the uses described below.

Looking first at FIG. 24, system 5 may be used to test for radon in air. In this form of the invention, sample box 15 contains two red "R" capsules 100R. Red "R" capsules 100R are removed from recesses 120 of sample box 15 and caps 130 are opened. Sample traps 135 are left inside red "R" capsules 100R. Sample traps 135 are placed 5 inches apart in the lowest level of the building to be tested for radon in the air. The room containing red "R" capsules 100R should have all windows and doors closed for a period of 48 hours. Sample box 15 is left in the room containing red "R" capsules 100R, and humidity indicator 122 and temperature indicator 123 are prepared for use (i.e., a humidity strip is removed from humidity indicator 122 and a temperature strip is removed from temperature indicator 123). After 48 hours, caps 130 of red "R" capsules 100R are closed, and red "R" capsules 100R are placed back into recesses 120 of sample box 15. The check-box 26 next to the red "R" circle 27R on chain-of-custody form 7 is checked and the humidity level (detected by humidity indicator 122) and the approximate temperature (detected by temperature indicator 123) are recorded on chain-of-custody form 7.

Looking now at FIG. 25, system 5 may also be used to test for contaminants in water. In this form of the invention, sample box 15 also contains two white "W" capsules 100W. White "W" capsules 100W are removed from recesses 120 of sample box 15 and caps 130 are removed. Each sample trap 135 is removed from a white "W" capsule 100W. Top seals 145 (i.e., caps) are removed from sample traps 135, sample traps 135 are placed under a cold water spigot which has been idle for at least 8 hours, and sample traps 135 are filled with cold water up to a demarcation line on sample traps 135. Top seals 145 (e.g., caps) are placed back onto sample traps 135 and white "W" capsules 100W are placed back into recesses 120 of sample box 15. The check-box 26 next to the white "W" circle 27W on chain-of-custody form 7 is checked.

Looking now at FIG. 26, system 5 may also be used to test for contaminants in outside air. In this form of the invention, sample box 15 also contains a yellow "Y" capsule 100Y marked "outside". It should be appreciated that the test for contaminants in outside air works best when started at room temperature. Yellow "outside" capsule 100Y is removed from recess 120 of sample box 15 and cap 130 is removed. Spore trap 135 is removed from yellow "outside" capsule 100Y. Base unit 10 is placed outside approximately three feet from the ground (preferably on a dry day) and plugged in. Top seal 145 and bottom seal 150 are peeled off of spore trap 135, and then spore trap 135 is loaded onto air input 35 of base unit 10 (with the arrow pointing down), ensuring that key notch 160 of spore trap 135 locks with key protrusion 92 of outer rim 80 of air input 35. Spore trap 135 should be pressed down firmly to ensure proper connection with air input 35 of base unit 10. Next, the yellow button marked "Y" of user interface 65 is pressed. Base unit 10 will run for 5 minutes at 15 LPM (see FIG. 14), beep and shut off. Then, spore trap 135 is removed from base unit 10, and top seal 145 and bottom seal 150 are placed back on the ends of spore trap 135. The re-sealed spore trap 135 is then placed back into yellow "outside" capsule 100Y, and yellow "outside" capsule 100Y is subsequently put into a recess 120 of sample box 15. The check-box 26 next to the yellow "Y" circle 27Y marked "outside" on chain-of-custody form 7 is checked.

Looking next at FIG. 27, system 5 may also be used to test for contaminants in air inside a home or office. In this form of the invention, sample box 15 also contains a yellow "Y" capsule 100Y marked "inside". Yellow "inside" capsule 100Y is removed from recess 120 of sample box 15 and cap 130 is removed. Spore trap 135 is removed from yellow "inside" capsule 100Y. Base unit 10 is placed in a desired testing area approximately three feet from the floor and plugged in. Top seal 145 and bottom seal 150 are peeled off of spore trap 135, and then spore trap 135 is loaded onto air input 35 of base unit 10 (with the arrow pointing down), ensuring that key notch 160 of spore trap 135 locks with key protrusion 92 of outer rim 80 of air input 35. Spore trap 135 should be pressed down firmly to ensure proper connection with air input 35 of base unit 10. Next, the yellow button marked "Y" of user interface 65 is pressed. Base unit 10 will run for 5 minutes at 15 LPM (see FIG. 14), beep and shut off. Then, spore trap 135 is removed from base unit 10, and top seal 145 and bottom seal 150 are placed back on the ends of spore trap 135. The re-sealed spore trap 135 is then placed back into yellow "inside" capsule 100Y, and yellow "inside" capsule 100Y is subsequently put into a recess 120 of sample box 15. The check-box 26 next to the yellow "Y" circle 27Y marked "inside" on chain-of-custody form 7 is checked.

Looking next at FIG. 28, system 5 may also be used to test for asbestos in air. In this form of the invention, sample box 15 also contains an orange "O" capsule 100O marked "asbestos". Orange "asbestos" capsule 100O is removed from recess 120 of sample box 15. In this form of the invention, fiber trap 135 comprises a bottom seal 150 only (i.e., fiber trap 135 does not comprise a top seal 145), and cap 130 comprises an adapter 105 for connection with air input 35 of base unit 10 (see FIGS. 18-21). Fiber trap 135 is removed from orange "asbestos" capsule 100O. Base unit 10 is placed in a desired testing area and plugged in. Bottom seal 150 (i.e., an end cap) is removed from fiber trap 135, and then fiber trap 135 is loaded onto air input 35 of base unit 10 via adapter 105 (with the arrow pointing down). Fiber trap 135 should be pressed down firmly to ensure proper connection with air input 35 of base unit 10. Next, the orange button marked "O" of user interface 65 is pressed. Base unit 10 will run for 15 minutes at 5 LPM (see FIG. 14), beep and shut off. Then, fiber trap 135 is removed from base unit 10, and bottom seal 150 is placed back on the end of fiber trap 135. The re-sealed fiber trap 135 is then placed back into orange "asbestos" capsule 100O, and orange "asbestos" capsule 100O is subsequently put into a recess 120 of sample box 15. The check-box 26 next to the orange "O" circle 270 marked "asbestos" on chain-of-custody form 7 is checked.

Figure 29:
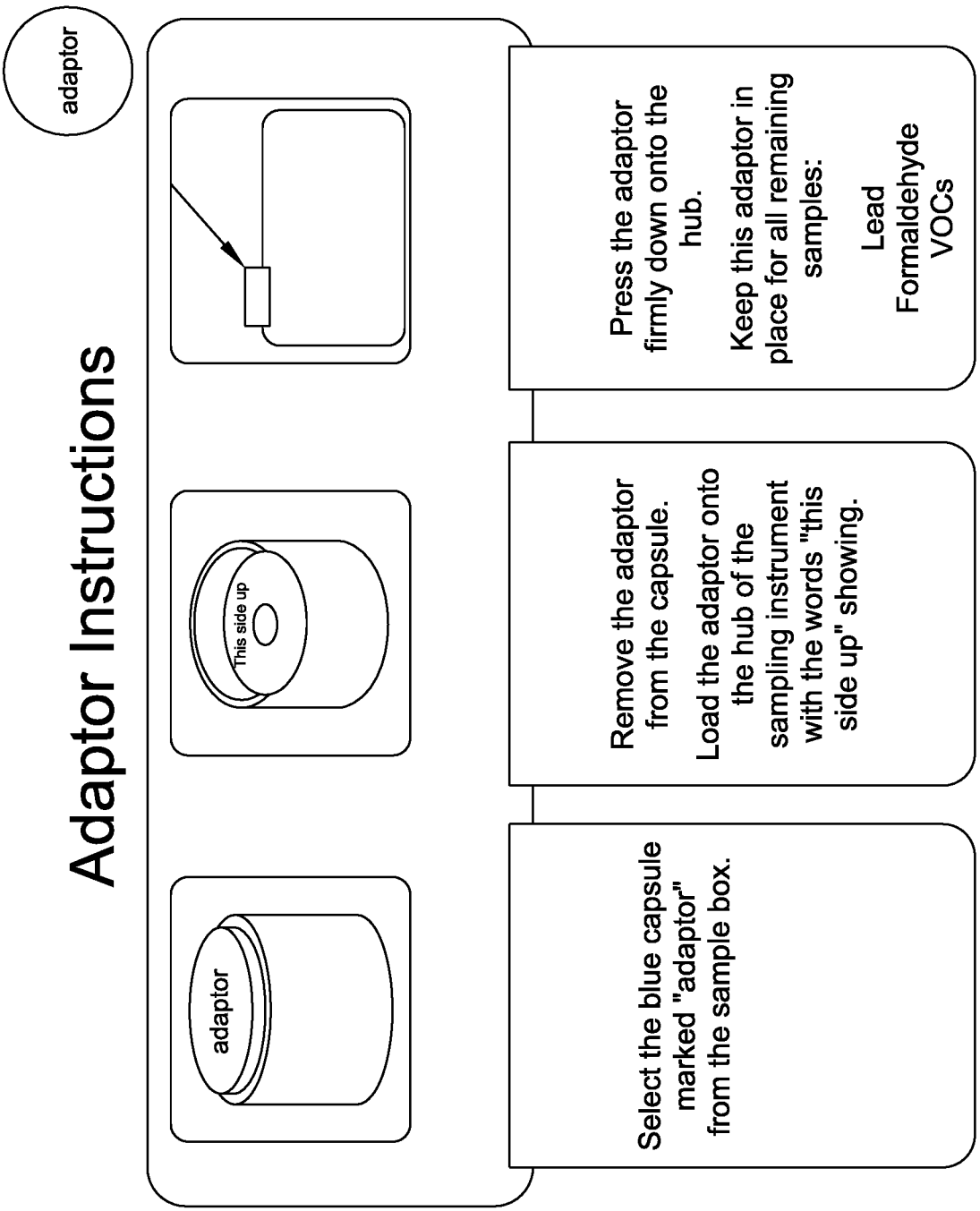

FIG. 29, shows how an adapter 105 may be used to connect a sample trap 135 to air input 35 of base unit 10.

Figure 30:
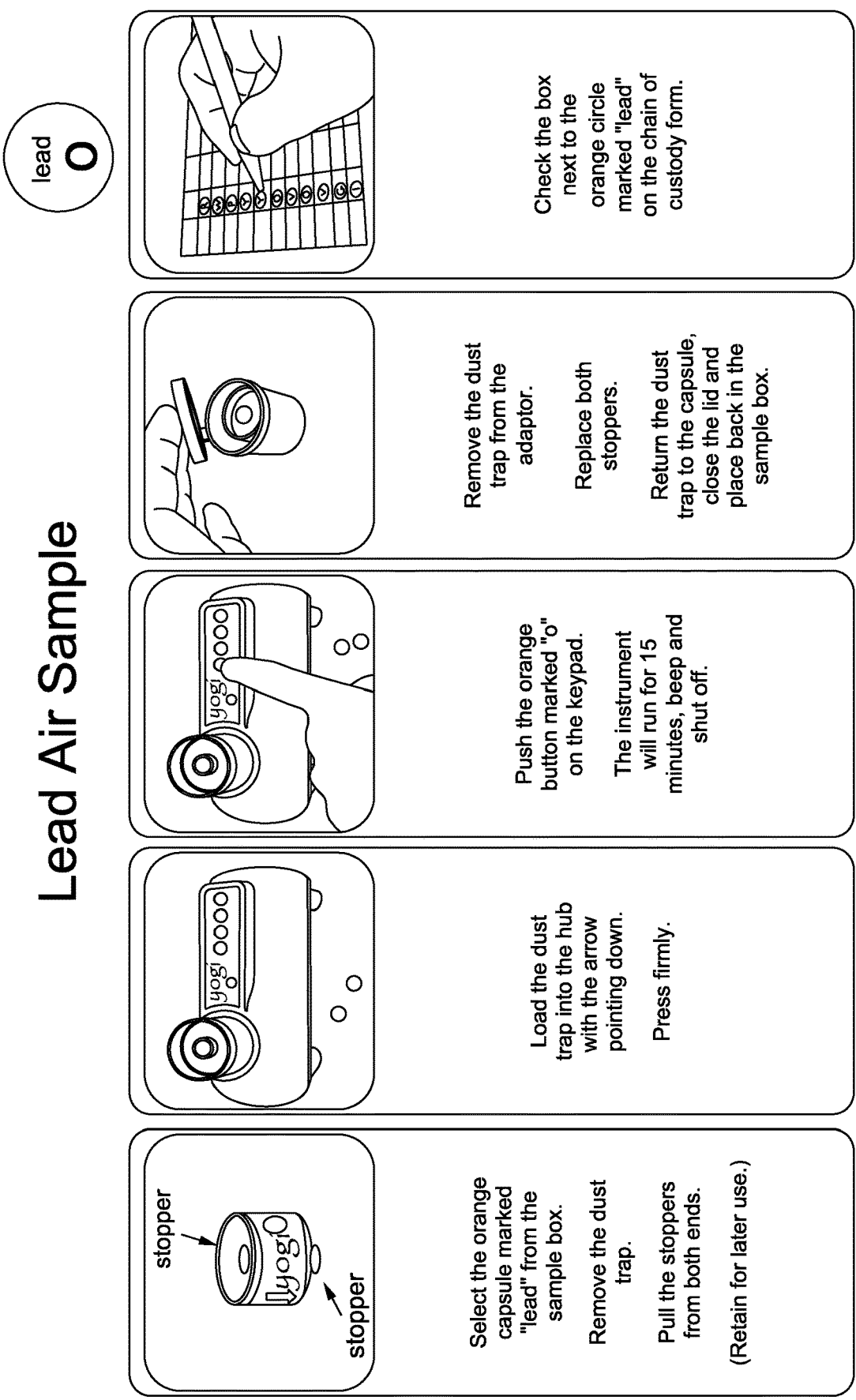

Looking next at FIG. 30, system 5 may also be used to test for lead in air. In this form of the invention, sample box 15 also contains an orange "O" capsule 100O marked "lead". Orange "lead" capsule 100O is removed from recess 120 of sample box 15 and cap 130 is removed. Dust trap 135 is removed from orange "lead" capsule 100O. Base unit 10 is placed in a desired testing area and plugged in. Adapter 105 is removed from sample box 15 and placed into air input 35 of base unit 10 (see FIG. 17). Top seal 145 (i.e., a stopper) and bottom seal 150 (i.e., a stopper) are removed from dust trap 135, and then dust trap 135 is loaded onto adapter 105 (with the arrow pointing down) (see FIG. 22). Dust trap 135 should be pressed down firmly to ensure proper connection with adapter 105. Next, the orange button marked "O" of user interface 65 is pressed. Base unit 10 will run for 15 minutes at 5 LPM (see FIG. 14), beep and shut off. Then, dust trap 135 is removed from base unit 10, and top seal 145 and bottom seal 150 are placed back on the ends of dust trap 135. The re-sealed dust trap 135 is then placed back into orange "lead" capsule 100O, and orange "lead" capsule 100O is subsequently put into a recess 120 of sample box 15. The check-box 26 next to the orange "O" circle 270 marked "lead" on chain-of-custody form 7 is checked. Note that adapter 105 may be left in place on air input 35 of base unit 10 for subsequent tests.

Figure 31:
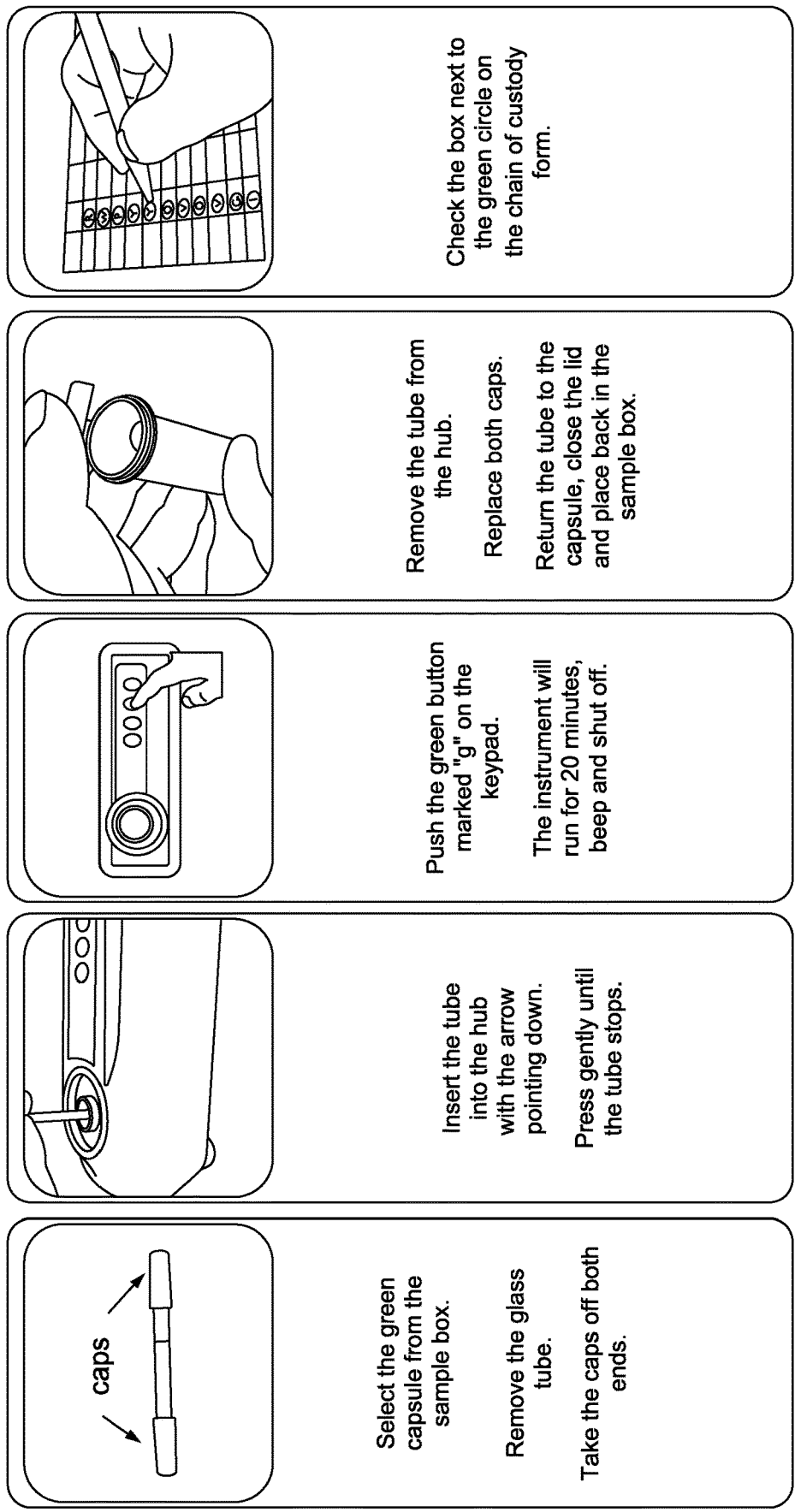

Looking next at FIG. 31, system 5 may also be used to test for formaldehyde in air. In this form of the invention, sample box 15 also contains a green "G" capsule 100G. Green "G" capsule 100G is removed from recess 120 of sample box 15 and cap 130 is removed. Glass tube trap 135 is removed from green "G" capsule 100G. Base unit 10 is placed in a desired testing area and plugged in. Top seal 145 (i.e., a cap) and bottom seal 150 (i.e., a cap) are removed from glass tube trap 135, and then glass tube trap 135 is loaded onto adapter 105 (with the arrow pointing down) (see FIG. 23). Glass tube trap 135 should be pressed down firmly to ensure proper connection with adapter 105. Next, the green button marked "G" of user interface 65 is pressed. Base unit 10 will run for 20 minutes at 0.2 LPM (see FIG. 14), beep and shut off. Then, glass tube trap 135 is removed from base unit 10, and top seal 145 and bottom seal 150 are placed back on the ends of glass tube trap 135. The re-sealed glass tube trap 135 is then placed back into green "G" capsule 100G, and green "G" capsule 100G is subsequently put into a recess 120 of sample box 15. The check-box 26 next to the green "G" circle 27G on chain-of-custody form 7 is checked. Note that adapter 105 may be left in place on air input 35 of base unit 10 for subsequent tests.

Looking now at FIG. 32, system 5 may also be used to test for volatile organic compounds (VOCs) in air. In this form of the invention, sample box 15 also contains an indigo "I" capsule 100I. Indigo "I" capsule 100I is removed from recess 120 of sample box 15 and cap 130 is removed. Glass tube trap 135 is removed from indigo "I" capsule 100I. Base unit 10 is placed in a desired testing area and plugged in. Top seal 145 (i.e., a cap) and bottom seal 150 (i.e., a cap) are removed from glass tube trap 135, and then glass tube trap 135 is loaded onto adapter 105 (with the arrow pointing down) (see FIG. 23). Glass tube trap 135 should be pressed firmly to ensure proper connection with adapter 105. Next, the indigo button marked "I" of user interface 65 is pressed. Base unit 10 will run for 2 hours at 0.2 LPM (see FIG. 14), beep and shut off. Then, glass tube trap 135 is removed from base unit 10, and top seal 145 and bottom seal 150 are placed back on the ends of glass tube trap 135. The re-sealed glass tube trap 135 is then placed back into indigo "I" capsule 100I, and indigo "I" capsule 100I is subsequently put into a recess 120 of sample box 15. The check-box 26 next to the indigo "I" circle 27I on chain-of-custody form 7 is checked.

After all desired tests have been run, preferably following the order listed in chain-of-custody form 7, adapter 105 may be left on base unit 10 or removed, but adapter 105 should remain with base unit 10 and should not be sent to the certified testing laboratory with sample box 15.

Lastly, chain-of-custody form 7 is placed inside sample box 15 and sample box 15 is sealed. Shipping label 25 is placed onto sample box 15 and sample box 15 is shipped to the certified testing laboratory.

6. Color-Coded and/or Letter-Coded System, and/or Other Coded Systems Using Numbers, Symbols and/or Other Markings As discussed above, some of the sample traps 135 contained within capsules 100 require different flow rates, and different flow durations, in order to provide reliable test results. By way of example but not limitation, in one preferred form of the invention, a sample trap 135 contained in a yellow "Y" capsule 100Y requires pump 45 to run for a duration of 5 minutes at a flow rate of 15 liters per minute (LPM); a sample trap 135 contained in an orange "O" capsule 100O requires pump 45 to run for a duration of 15 minutes at a flow rate of 5 LPM; a sample trap 135 contained in a green "G" capsule 100G requires pump 45 to run for a duration of 20 minutes at a flow rate of 0.2 LPM; and a sample trap 135 contained in an indigo "I" capsule 100I requires pump 45 to run for a duration of 2 hours at a flow rate of 0.2 LPM. In order to simplify operation for the user, user interface 65 comprises 4 color-coded and/or letter-coded buttons 66, wherein each color-coded and/or letter-coded button 66 activates pump 45 with the specific mode of operation required for the sample trap 135 contained in a similarly color-coded and/or letter-coded capsule 100.

In accordance with the present invention, in one form of the invention, the aforementioned color-coding scheme, and/or the aforementioned letter-coding scheme, is used to link the specific sample traps 135 contained within specific capsules 100 to specific buttons 66 of user interface 65 of base unit 10, with those specific buttons 66 in turn being linked to specific modes of operation for pump 45 via CPU 60, whereby to link specific modes of operation of pump 45 to specific sample traps 135 contained within specific capsules 100.

Note that where a letter-coding scheme is used, the letters may be from the conventional Latin alphabet, or from another alphabet, e.g., the Greek alphabet.

It should also be appreciated that other coding schemes may be used to link specific sample traps 135 contained within specific capsules 100 to specific buttons 66 of user interface 65 of base unit 10, with those specific buttons 66 in turn being linked to specific modes of operation for pump 45 via CPU 60, whereby to link specific modes of operation of pump 45 to specific sample traps 135 contained within specific capsules 100.

By way of example but not limitation, a unifying "number-coding" scheme may also be incorporated in system 5.

More particularly, in this form of the invention, the different buttons 66 of user interface 65 are correlated to the different capsules 100 using a number-coding scheme. In other words, when using a "1" capsule, the "1" button is pressed to cause pump 45 to run for the appropriate duration for the "1" capsule; when using a "2" capsule, the "2" button is pressed to cause pump 45 to run for the appropriate duration for the "2" capsule; when using a "3" capsule, the "3" button is pressed to cause pump 45 to run for the appropriate duration for the "3" capsule; and when using a "4" capsule, the "4" button is pressed to cause pump 45 to run for the appropriate duration for the "4" capsule.

This same approach may be carried across to the circles 27 on chain-of-custody form 7, e.g., a given test may have a "1" circle next to it, or a "2" circle next to it, or a "3" circle next to it, or a "4" circle next to it.

Preferably the number-coding scheme is used simultaneously with the aforementioned color-coding scheme.

Thus, in one preferred form of the invention, each circle 27 on chain-of-custody form 7 is color-coded and number-coded to a particular capsule 100 (i.e., a particular environmental test) and, where appropriate, is color-coded and number-coded to a particular button on user interface 65. The color-coded and number-coded button 66 on user interface 65 corresponds to a specific mode of operation (i.e., to specific pump operational parameters) stored in CPU 60, with the color-coding and number-coding ensuring that each environmental test is run under optimal pump conditions for collecting a particular sample. The appropriate check-box 26 corresponding to a color-coded and number-coded circle 27 of chain-of-custody form 7 is filled out and, once all tests are complete, sample box 15 is sent to a certified laboratory for testing.

By way of example but not limitation, a test for contaminants in air may be contained in a capsule 100 with a yellow cap 130 marked with the number "1", which corresponds to a section of chain-of-custody form 7 marked with the number "1" contained within a yellow circle 27, and which corresponds to a yellow button 66 marked with the number "1" on user interface 65 of base unit 10. Similarly, a test for contaminants in air may be contained in a capsule 100 with an orange cap 130 marked with the number "2", which corresponds to a section of chain-of-custody form 7 marked with the number "2" contained within an orange circle 27, and which corresponds to an orange button 66 marked with the number "2" on user interface 65 of base unit 10. And a test for contaminants in air may be contained in a capsule 100 with a green cap 130 marked with the number "3", which corresponds to a section of chain-of-custody form 7 marked with the number "3" contained within a green circle 27, and which corresponds to a green button 66 marked with the number "3" on user interface 65 of base unit 10. And a test for contaminants in air may be contained in a capsule 100 with an indigo cap 130 marked with the number "4", which corresponds to a section of chain-of-custody form 7 marked with the number "4" contained within an indigo circle 27, and which corresponds to an indigo button 66 marked with the number "4" on user interface 65 of base unit 10.

It should also be appreciated that still other coding schemes may be used to link specific sample traps 135 contained within specific capsules 100 to specific buttons 66 of user interface 65 of base unit 10, with those specific buttons 66 in turn being linked to specific modes of operation for pump 45 via CPU 60, whereby to link specific modes of operation of pump 45 to specific sample traps 135 contained within specific capsules 100.

By way of further example but not limitation, a unifying "symbol-coding" and/or other marking scheme may be incorporated in system 5. In this form of the invention, the letters of the letter-coded system, and/or the numbers of the number-coded system, are replaced by symbols, e.g., *, #, +, etc., and/or other markings. Preferably the aforementioned color-coded system is used in conjunction with such a symbol-coded system, i.e., each circle 27 of chain-of-custody form 7, each capsule 100 and each button 66 has both colors and symbols to guide operation of system 5.

It will be appreciated that the unifying letter-coding scheme, number-coding scheme, symbol-coding scheme and/or other marking scheme incorporated in system 5 (i.e., the letter-coding, number-coding, symbol-coding and/or other marking scheme of chain-of-custody form 7; the letter-coding, number-coding, symbol-coding and/or other marking scheme of capsules 100; and the letter-coding, number-coding, symbol-coding and/or other marking scheme of user interface 65) allows a color-blind user to easily perform multiple environmental tests while still obtaining high quality and accurate tests results.

7. Alternative Base Unit

Figure 33:
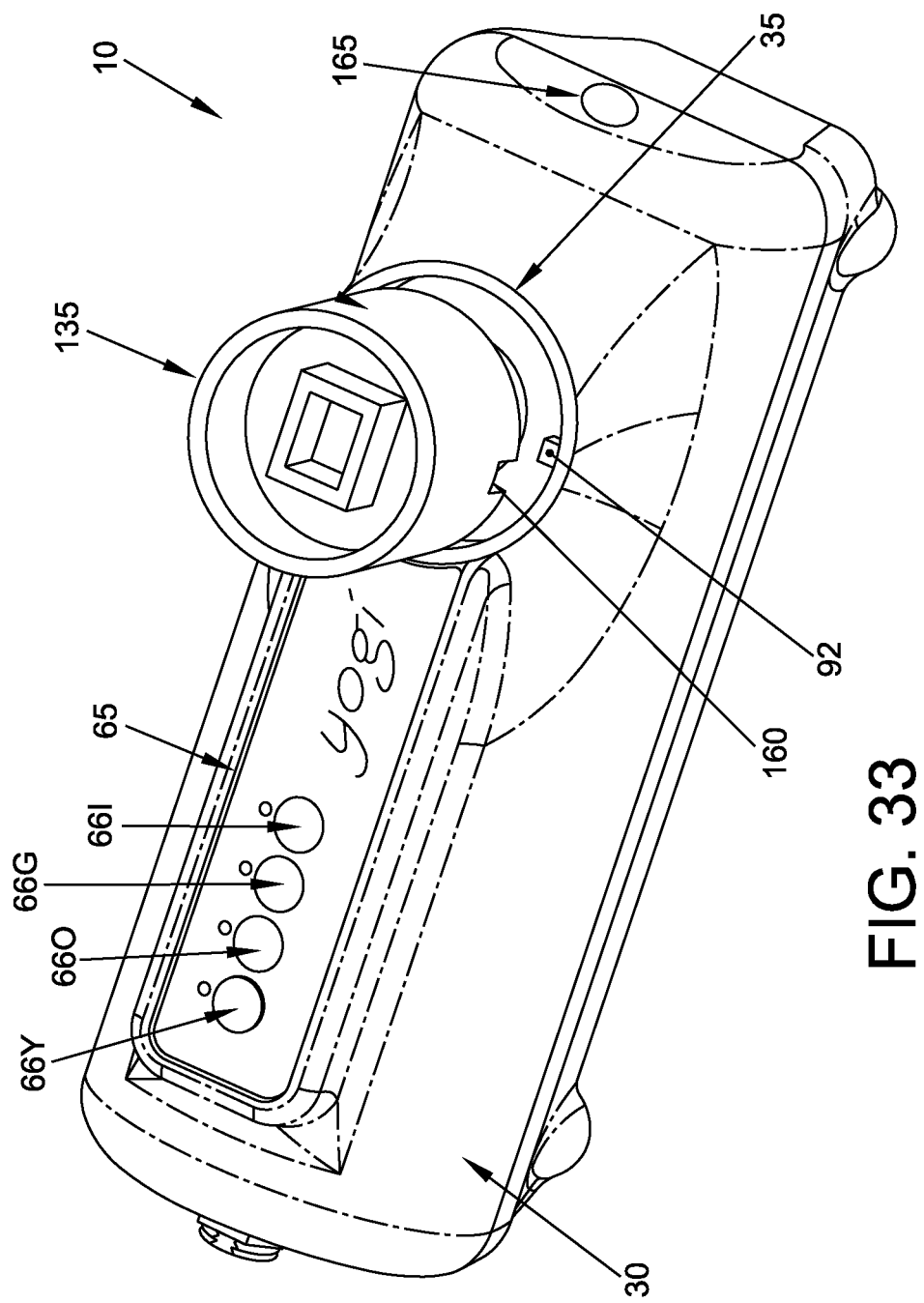
FIG. 33 is a schematic view showing details of an alternative base unit formed in accordance with the present invention.
Figure 35:
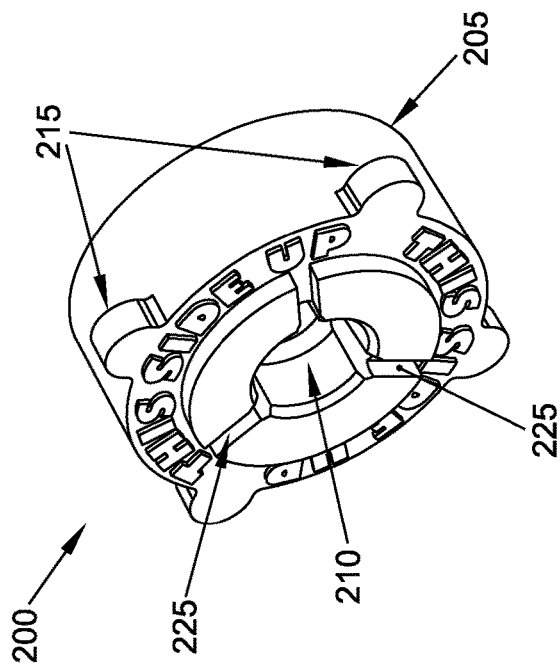
Figure 34:
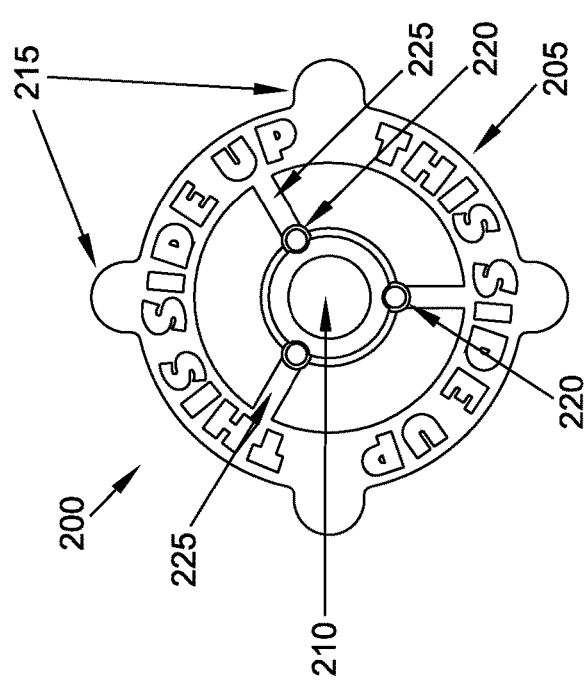
Figure 36:
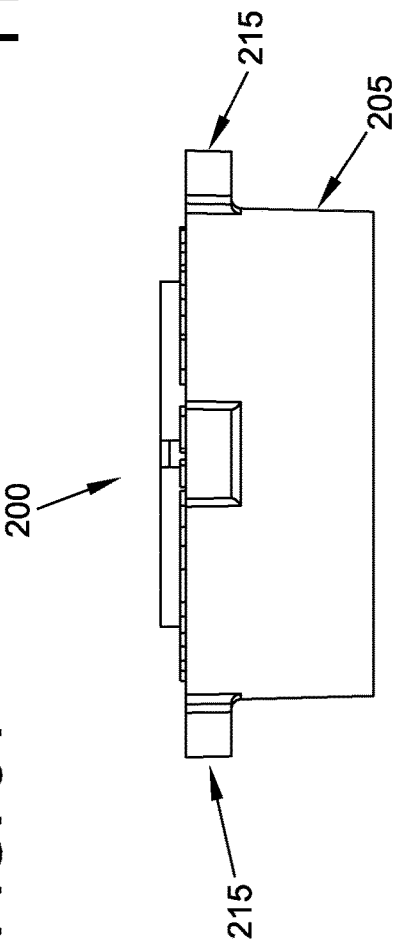

In one form of the invention, base unit 10 further comprises a permanent volatile organic compounds (VOCs) monitor 165 in order to provide immediate reading on VOCs present in the air. See, for example, FIG. 33.

8. Alternative Adapter

It should be appreciated that some environmental tests require very low flow rates, with high precision, in order to provide highly reliable results. It should also be appreciated that it can be difficult to operate pump 45 with these very low flow rates while maintaining high precision.

To this end, in another preferred form of the present invention, and looking now at FIGS. 34-42, an adapter 200 may be provided which enables pump 45 to be run at faster speeds but still provide very low flow rates to sample traps 135 while maintaining high precision. More particularly, in this form of the invention, adapter 200 is provided for sample traps 135 which require low sample trap flow rates (e.g., 5 LPM, or more preferably 3 LPM, to test for lead in air, and 0.2 LPM to test for formaldehyde in air and to test for volatile organic compounds (VOCs) in air).

One end of adapter 200 is designed to mount to air input 35 of base unit 10 by fitting between outer rim 80 and inner rim 85 (i.e., in recess 90) of air input 35 of base unit 10. The other end of adapter 200 seats a sample trap 135 thereon. More particularly, adapter 200 generally comprises a body 205 and an opening 210. Body 205 generally comprises tabs 215, vent holes 220 and vent slots 225.

It should be appreciated that vent holes 220 and/or vent slots 225 create deliberate leak paths ("weepholes") so as to enable pump 45 to be run at higher speeds (and thus have a higher performance accuracy) while still providing the low air flow rate needed for a particular test (i.e., a test for lead in air, a test for formaldehyde in air, a test for volatile organic compounds (VOCs) in air, etc.).

By way of example but not limitation, when pump 45 is used to test for lead in air (requiring a flow rate of 5 LPM, or more preferably 3 LPM), to test for formaldehyde in air (requiring a flow rate of 0.2 LPM) or to test for volatile organic compounds (VOCs) in air (requiring a flow rate of 0.2 LPM), pump 45 may be run at a higher pump rate (e.g., 8 LPM for lead, and 1.0 LPM for formaldehyde and VOCs) and the leak created by vent holes 220 and/or vent slots 225 will appropriately reduce the air flow rate experienced by sample trap 135 (i.e., the air flow rate experienced by sample trap 135 will be reduced to 3 LPM for lead or to 0.2 LPM for formaldehyde and VOCs). In this way, peak performance of pump 45 is achieved while maintaining the integrity of all of the environmental tests run on base unit 10.

More particularly, when pump 45 is used to test for lead in air (see FIGS. 37-39), adapter 200 is seated on air input 35 of base unit 10, and body 140C of a lead sample trap 135 is seated on adapter 200, with vent slots 225 creating an air vent path between adapter 200 and body 140C of sample trap 135, whereby to allow air flow (i) between body 140C of sample trap 135 and outer rim 80 of air input 35, and to flow through vent slots 225 of adapter 200, (ii) through vent holes 220 of adapter 200, and (iii) into opening 75 of air input 35 of base unit 10. As a result, pump 45 may be run at higher speeds (and thus have higher performance accuracy) while still providing the low airflow rate needed for a lead test.

When pump 45 is used to test for formaldehyde and/or VOCs in air (see FIGS. 40-42), adapter 200 is seated on air input 35 of base unit 10, and body 140D of a formaldehyde and/or VOCs sample trap 135 is seated on adapter 200, with vent holes 220 creating an air vent path between adapter 200 and body 140D of sample trap 135, whereby to allow air flow (i) between body 140D of sample trap 135 and vent holes 220 of adapter 200, and (ii) into opening 75 of air input 35 of base unit 10. As a result, pump 45 may be run at higher speeds (and thus have higher performance accuracy) while still providing the low airflow rate needed for a lead test.

The following table shows one preferred scheme for using pump 45 to draw air through sample traps 135 testing for mold, asbestos, lead, formaldehyde and VOCs, using no adapter, a non-leaky adapter, and a leaky adapter, as shown:

| Contaminant | Capsule and Button Marking Scheme | Adapter ? | Pump Flow Rate (LPM) | Leaky Adapter Weephole Flow Rate (LPM) | Sample Trap Flow Rate (LPM) | Pump Time Duration (min) | Air Volume Through Sample Trap (L) |
|---|---|---|---|---|---|---|---|
| Mold | Yellow "Y" | No | 15 | N/A | 15 | 5 | 75 |
| Asbestos | Orange "O" | 90° elbow adapter (non-leaky) | 8 | N/A | 8 | 40 | 320 |
| Lead | Orange "O" | leaky adapter | 8 | 5 | 3 | 40 | 120 |
| Formaldehyde | Green "G" | leaky adapter | 1.0 | 0.8 | 0.2 | 20 | 4 |
| VOCs | Indigo "I" | leaky adapter | 1.0 | 0.8 | 0.2 | 30 | 6 |

(Note that the sample trap flow rates shown in the preceding table differ somewhat from the sample trap flow rates shown in FIG. 14, and illustrate another preferred form of the present invention.)

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A system for assessing the quality of air and/or drinking water, said system comprising:
   a plurality of sample traps, wherein each of said sample traps is configured to test for a different environmental contaminant, and further wherein at least some of said sample traps require air to be drawn through that sample trap at a particular rate, and for a particular time duration, in order to properly test for a particular environmental contaminant;
   a base unit, said base unit comprising:
      a pump for drawing air;
      a mount for connecting a sample trap to said pump so as to draw air through that sample trap when said pump is operated;
      a central processing unit (CPU) pre-programmed to operate said pump in a plurality of modes of operation, wherein each mode of operation causes said pump to draw air at a particular pump rate, and for a particular pump time duration; and
      a plurality of buttons communicating with said CPU, wherein activating a particular button causes said CPU to operate said pump in a particular mode of operation; and
   a marking scheme comprising a plurality of unique markings, wherein each of said buttons is marked with a different unique marking, and further wherein each of said at least some of said sample traps is marked with the same unique marking as the button which causes said pump to operate in the particular mode of operation required to draw air through that sample trap at the particular rate, and for the particular time duration, required for that sample trap to properly test for a particular environmental contaminant.

2. A system according to claim 1 wherein said plurality of unique markings comprise different colors.

3. A system according to claim 1 wherein said plurality of unique markings comprise different letters.

4. A system according to claim 1 wherein said plurality of unique markings comprise different numbers.

5. A system according to claim 1 wherein said plurality of unique markings comprise different symbols.

6. A system according to claim 1 wherein said plurality of unique markings comprise a combination of different colors and different letters, numbers or symbols.

7. A system according to claim 1 further comprising a plurality of capsules for receiving said plurality of sample traps.

8. A system according to claim 7 wherein each of said at least some of said sample traps is marked by marking its associated capsule.

9. A system according to claim 7 wherein said plurality of sample traps are adapted to test for environmental contaminants selected from the group consisting of radon, contaminants in water, outside air contaminants, inside air contaminants, asbestos, lead, formaldehyde and volatile organic compounds (VOCs).

10. A system according to claim 7 wherein said at least some of said sample traps are adapted to test for outside air contaminants, inside air contaminants, asbestos, lead, formaldehyde and volatile organic compounds (VOCs).

11. A system according to claim 1 wherein said central processing unit (CPU) is configured to operate said pump using pulse width modulated (PWM) digital signals.

12. A system according to claim 1 wherein said central processing unit (CPU) is pre-programmed to operate said pump in four modes of operation.

13. A system according to claim 12 wherein said four modes of operation are: (i) drawing air at a rate of 15 liters per minute (LPM) for a duration of 5 minutes; (ii) drawing air at a rate of 5 liters per minute (LPM) for a duration of 15 minutes; (iii) drawing air at a rate of 0.2 liters per minute (LPM) for a duration of 20 minutes; and (iv) drawing air at a rate of 0.2 liters per minute (LPM) for a duration of 120 minutes.

14. A system according to claim 12 wherein said four modes of operation are: (i) drawing air at a rate of 15 liters per minute (LPM) for a duration of 5 minutes; (ii) drawing air at a rate of 8 liters per minute (LPM) for a duration of 40 minutes; (iii) drawing air at a rate of 1.0 liters per minute (LPM) for a duration of 20 minutes; and (iv) drawing air at a rate of 1.0 liters per minute (LPM) for a duration of 30 minutes.

15. A system according to claim 1 further comprising an adapter for connecting a sample trap to said mount.

16. A system according to claim 15 wherein said adapter comprises a leaky adapter, such that, when said leaky adapter is mounted to said mount and a sample trap is mounted to said leaky adapter, air is drawn into said pump at a rate faster than air is drawn through said sample trap.

17. A system according to claim 16 wherein a mode of operation of said pump takes into account that a sample trap is mounted to said pump using said leaky adapter.

18. A system according to claim 1 further comprising a list comprising a plurality of tests which are to be conducted.

19. A system according to claim 18 wherein said list is ordered in the order in which the tests are to be conducted.

20. A system according to claim 19 wherein the order of said list is inversely related to the pump speed required to conduct a particular test.

21. A system according to claim 19 wherein the order of said list is inversely related to the pump run time required to conduct a particular test.

22. A system according to claim 18 wherein each test on said list is marked with the same unique marking as the sample trap to be used for that test.

23. A system according to claim 18 wherein said list is a check-list.

24. A system according to claim 7 further comprising a sample box containing said base unit and said capsules.

25. A system according to claim 24 further comprising a mailing label.

26. A method for assessing the quality of air and/or drinking water, the method comprising:
providing a system, said system comprising:
a plurality of sample traps, wherein each of said sample traps is configured to test for a different environmental contaminant, and further wherein at least some of said sample traps require air to be drawn through that sample trap at a particular rate, and for a particular time duration, in order to properly test for a particular environmental contaminant;
a base unit, said base unit comprising:
a pump for drawing air;
a mount for connecting a sample trap to said pump so as to draw air through that sample trap when said pump is operated;
a central processing unit (CPU) pre-programmed to operate said pump in a plurality of modes of operation, wherein each mode of operation causes said pump to draw air at a particular pump rate, and for a particular pump time duration; and
a plurality of buttons communicating with said CPU, wherein activating a particular button causes said CPU to operate said pump in a particular mode of operation; and
a marking scheme comprising a plurality of unique markings, wherein each of said buttons is marked with a different unique marking, and further wherein each of said at least some of said sample traps is marked with the same unique marking as the button which causes said pump to operate in the particular mode of operation required to draw air through that sample trap at the particular rate, and for the particular time duration, required for that sample trap to properly test for a particular environmental contaminant;
mounting a sample trap to said pump; and
activating the button having the same unique marking as the sample trap mounted to said pump.

27. A method according to claim 26 further comprising:
dismounting the sample trap from said pump; and
mounting a different sample trap to said pump; and
activating the button having the same unique marking as the different sample trap mounted to said pump.

28. A method according to claim 26 wherein said plurality of unique markings comprise at least one selected from the group consisting of different colors, different letters, different numbers and different symbols.

29. A method according to claim 26 wherein said plurality of unique markings comprise a combination of different colors and different letters, numbers or symbols.

30. A method according to claim 26 further comprising a plurality of capsules for receiving said plurality of sample traps, wherein each of said at least some of said sample traps is marked by marking its associated capsule, and further comprising removing a sample trap prior to mounting the sample trap to said pump.

31. A method according to claim 30 further comprising sealing a sample trap in its associated capsule after removing the sample trap from said pump.

32. A method according to claim 26 wherein said pump is pre-calibrated so as to achieve precise performance characteristics.

33. A method according to claim 32 wherein said pump comprises a motor and an associated printed circuit board (PCB) for controlling operation of said motor and hence operation of said pump, and further wherein said pump is pre-calibrated by:
mounting a sample trap to said pump;
operating said pump by driving said motor at the motor speed expected to achieve a desired sample trap flow rate;
determining the actual flow rate passing through the sample trap when said motor is driven at the motor speed expected to achieve a desired sample trap flow rate;
comparing the actual flow rate passing through the sample trap with the desired sample trap flow rate; and
adjusting the motor speed as necessary so as to enable the motor to achieve the desired sample trap flow rate.

34. A method according to claim 26 wherein said central processing unit (CPU) is pre-programmed to operate said pump in four modes of operation.

35. A method according to claim 34 wherein said four modes of operation are: (i) drawing air at a rate of 15 liters per minute (LPM) for a duration of 5 minutes; (ii) drawing air at a rate of 5 liters per minute (LPM) for a duration of 15 minutes; (iii) drawing air at a rate of 0.2 liters per minute (LPM) for a duration of 20 minutes; and (iv) drawing air at a rate of 0.2 liters per minute (LPM) for a duration of 120 minutes.

36. A method according to claim 34 wherein said four modes of operation are: (i) drawing air at a rate of 15 liters per minute (LPM) for a duration of 5 minutes; (ii) drawing air at a rate of 8 liters per minute (LPM) for a duration of 40 minutes; (iii) drawing air at a rate of 1.0 liters per minute (LPM) for a duration of 20 minutes; and (iv) drawing air at a rate of 1.0 liters per minute (LPM) for a duration of 30 minutes.

37. A method according to claim 26 further comprising an adapter for connecting a sample trap to said mount.

38. A method according to claim 37 wherein said adapter comprises a leaky adapter, such that, when said leaky adapter is mounted to said mount and a sample trap is mounted to said leaky adapter, air is drawn into said pump at a rate faster than air is drawn through said sample trap.

39. A method according to claim 38 wherein a mode of operation of said pump takes into account that a sample trap is mounted to said pump using said leaky adapter.

40. A method according to claim 26 further comprising a list comprising a plurality of tests which are to be conducted, wherein said list is ordered in the order in which the tests are to be conducted.

41. A method according to claim 40 wherein the order of said list is inversely related to the pump speed required to conduct a particular test.

42. A method according to claim 40 wherein the order of said list is inversely related to the pump run time required to conduct a particular test.

43. A method according to claim 40 wherein each test on said list is marked with the same unique marking as the sample trap to be used for that test.

44. A method according to claim 40 wherein said list is a check-list.

45. A method according to claim 26 further comprising a sample box containing said base unit and said capsules, and further wherein said sample box is sealed and mailed to a lab after all of the tests have been completed.

\* \* \* \* \*